(12) United States Patent
Chen et al.

(10) Patent No.: US 11,078,194 B2
(45) Date of Patent: Aug. 3, 2021

(54) SALT FORM AND CRYSTAL FORM SERVING AS FGFR AND VEGFR INHIBITOR COMPOUNDS, AND PREPARATION METHOD THEREFOR

(71) Applicant: HARBIN ZHENBAO PHARMACEUTICAL CO., LTD., Heilongjiang (CN)

(72) Inventors: Zhengxia Chen, Shanghai (CN); Yang Zhang, Shanghai (CN); Meibi Dai, Shanghai (CN); Hongfei Cheng, Shanghai (CN); Suqin Yang, Shanghai (CN); Wenju Li, Shanghai (CN); Jian Li, Shanghai (CN); Shuhui Chen, Shanghai (CN)

(73) Assignee: HARBIN ZHENBAO PHARMACEUTICAL CO., LTD., Heilongjiang (CN)

(*) Notice: Subject to any disclaimer, the term of this patent is extended or adjusted under 35 U.S.C. 154(b) by 0 days.

(21) Appl. No.: 16/770,196

(22) PCT Filed: Dec. 7, 2018

(86) PCT No.: PCT/CN2018/119716
§ 371 (c)(1),
(2) Date: Jun. 29, 2020

(87) PCT Pub. No.: WO2019/109995
PCT Pub. Date: Jun. 13, 2019

(65) Prior Publication Data
US 2020/0361913 A1    Nov. 19, 2020

(30) Foreign Application Priority Data

Dec. 7, 2017    (CN) .......................... 201711286398.X

(51) Int. Cl.
| C07D 405/14 | (2006.01) |
| C07D 401/14 | (2006.01) |
| C07D 413/14 | (2006.01) |
| C07D 401/12 | (2006.01) |
| A61P 35/00 | (2006.01) |
| A61K 31/416 | (2006.01) |

(52) U.S. Cl.
CPC ............ C07D 405/14 (2013.01); A61P 35/00 (2018.01)

(58) Field of Classification Search
CPC .. C07D 405/14; C07D 401/14; C07D 413/14; C07D 401/12; C07D 403/02;
(Continued)

(56) References Cited

U.S. PATENT DOCUMENTS

| 10,519,133 B2 * | 12/2019 | Chen ..................... A61K 31/395 |
| 2009/0054397 A1 | 2/2009 | Ohi et al. |
| 2018/0222886 A1 | 8/2018 | Chen et al. |

FOREIGN PATENT DOCUMENTS

| CN | 201711286398.X | 12/2017 |
| EP | 3333157 A1 | 6/2018 |

(Continued)

OTHER PUBLICATIONS

Dec. 7, 2018 International Search Report issued in International Patent Application No. PCT/CN2018/119716.
(Continued)

Primary Examiner — Niloofar Rahmani
(74) Attorney, Agent, or Firm — Harness, Dickey & Pierce, P.L.C.

(57) ABSTRACT

Disclosed in the present invention are a salt form and a crystal form serving as FGFR and VEGFR inhibitor compounds, a preparation method therefor, and medical uses thereof.

(Continued)

-continued (IV)

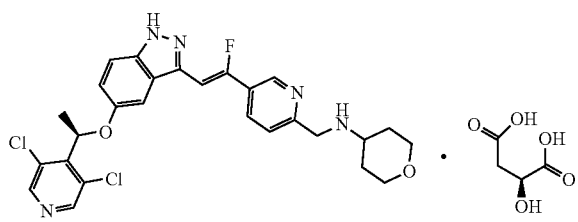

10 Claims, 24 Drawing Sheets

(58) Field of Classification Search
CPC ..... C07D 401/02; C07D 403/14; A61P 35/00; A61K 31/416; A61K 31/395
USPC .......................................................... 514/333
See application file for complete search history.

(56) References Cited

FOREIGN PATENT DOCUMENTS

| WO | WO-02/10137 A2 | 2/2002 |
| WO | WO-2002/022598 A1 | 3/2002 |
| WO | WO-2003/101968 A1 | 12/2003 |
| WO | 2017024968 | * 2/2017 |
| WO | WO-2017024968 A1 | 2/2017 |

OTHER PUBLICATIONS

Dec. 7, 2018 Written Opinion of the International Searching Authority issued in International Patent Application No. PCT/CN2018/119716.

Caira, Mino R. "Crystalline Polymorphism of Organic Compounds." Topics in Current Chemistry, 1998, pp. 163-208. Crossref, doi:10.1007/3-540-69178-2_5.

Partial Supplementary European search report issued in European Patent Application No. 18886074.6, dated Dec. 9, 2020.

May 27, 2021 Japanese Notice of reasons of refusal issued in Japanese Patent Application No. 2020531456.

* cited by examiner

SALT FORM AND CRYSTAL FORM SERVING AS FGFR AND VEGFR INHIBITOR COMPOUNDS, AND PREPARATION METHOD THEREFOR

CROSS-REFERENCE TO RELATED APPLICATIONS

This application is a 371 National Phase of International Application No. PCT/CN2018/119716, filed Dec. 7, 2018, which claims the benefit of Chinese Patent Application No. CN 201711286398.X, filed Dec. 7, 2017. The entire disclosures of the above applications are incorporated herein by reference.

FIELD OF INVENTION

The invention relates to crystal forms serving as FGFR and VEGFR inhibitor compounds, and preparation method therefor.

PRIOR ARTS

Fibroblast growth factor (FGF) has been recognized as an important mediator of many physiological processes, such as morphogenesis during development and angiogenesis. The fibroblast growth factor receptor (FGFR) family consists of four members (FGFR1-FGFR4), which are glycoproteins composed of extracellular immunoglobulin (Ig)-like domains, a hydrophobic transmembrane region and a cytoplasmic part containing a tyrosine kinase domain. FGF binding leads to FGFR dimerization, followed by receptor autophosphorylation and activation of downstream signaling pathways. Receptor activation is sufficient for the recovery and activation of specific downstream signaling partners that participate in the regulation of diverse processes such as cell growth, cell metabolism and cell survival. Thus, the FGF/FGFR signaling pathway has pleiotropic effects on many biological processes critical to tumor cell proliferation, migration, invasion, and angiogenesis.

Vinyl indazoles are known in the art for the treatment of cancer. See for example, WO0210137 and WO2003101968. FGFR inhibitors are also known in the art. See for example, WO2002022598.

CONTENT OF THE PRESENT INVENTION

The present disclosure provides a crystal form A of a compound of formula (I), wherein the X-ray powder diffraction pattern thereof comprises characteristic diffraction peaks at the following angle 2θ: 5.26±0.2°, 10.47±0.2°, and 20.98±0.2°.

(I)

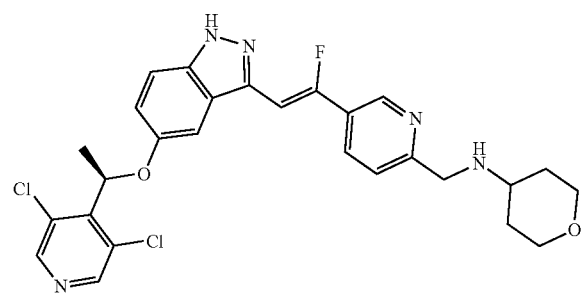

In some embodiments of the present disclosure, the X-ray powder diffraction pattern of the crystal form A comprises characteristic diffraction peaks at the following angle 2θ: 5.26±0.2°, 7.65±0.2°, 10.47±0.2°, 19.74±0.2°, 20.33±0.2°, 20.98±0.2°, 26.30±0.2°, and 26.91±0.2°.

In some embodiments of the present disclosure, the XRPD pattern of the crystal form A is as shown in FIG. 1.

In some embodiments of the present disclosure, the analytical data of the XRPD pattern of the crystal form A is as shown in Table 1:

TABLE 1

| | XRPD diffraction data of the crystal form A of the compound of formula (I) | | |
|---|---|---|---|
| No. | 2θ Angle (°) | d-spacing (Å) | Relative intensity (%) |
| 1 | 5.26 | 16.7873 | 36.4 |
| 2 | 7.651 | 11.5456 | 11 |
| 3 | 8.376 | 10.5482 | 2 |
| 4 | 8.52 | 10.3694 | 2.8 |
| 5 | 9.247 | 9.5557 | 3.5 |
| 6 | 10.467 | 8.4447 | 29.8 |
| 7 | 11.209 | 7.8869 | 2.4 |
| 8 | 11.553 | 7.6532 | 2.6 |
| 9 | 11.867 | 7.4515 | 2.6 |
| 10 | 12.359 | 7.1558 | 3.4 |
| 11 | 14.06 | 6.2937 | 2.7 |
| 12 | 14.667 | 6.0348 | 3 |
| 13 | 15.713 | 5.6353 | 6.6 |
| 14 | 16.091 | 5.5036 | 5.1 |
| 15 | 16.778 | 5.2799 | 11.4 |
| 16 | 18.515 | 4.7882 | 3.5 |
| 17 | 18.794 | 4.7177 | 4 |
| 18 | 19.286 | 4.5985 | 5.2 |
| 19 | 19.738 | 4.4941 | 13.4 |
| 20 | 20.328 | 4.365 | 16.3 |
| 21 | 20.98 | 4.2307 | 100 |
| 22 | 21.728 | 4.0868 | 2.5 |
| 23 | 22.067 | 4.0248 | 2.3 |
| 24 | 22.974 | 3.8679 | 3.8 |
| 25 | 23.311 | 3.8128 | 6.4 |
| 26 | 23.78 | 3.7387 | 2.4 |
| 27 | 25.319 | 3.5148 | 9.4 |
| 28 | 25.928 | 3.4336 | 6.5 |
| 29 | 26.303 | 3.3855 | 23.7 |
| 30 | 26.912 | 3.3102 | 11.1 |
| 31 | 27.746 | 3.2126 | 4 |
| 32 | 28.101 | 3.1728 | 5.2 |
| 33 | 29.44 | 3.0315 | 1.3 |
| 34 | 30.311 | 2.9463 | 2.3 |
| 35 | 37.582 | 2.3913 | 1.8 |

In some embodiments of the present disclosure, the differential scanning calorimetry curve of the crystal form A has an onset point of an endothermic peak at 42.97° C.±3° C., 139.63° C.±3° C. and 203.56° C.±3° C. respectively, and has an onset point of an exothermic peak at 147.45° C.±3° C.

In some embodiments of the present disclosure, the DSC pattern of the crystal form A is as shown in FIG. 2.

In some embodiments of the present disclosure, the thermogravimetric analysis curve of the crystal form A has a weight loss of 7.074% occurred at 120.00° C.±3° C. and a weight loss of 0.4317% occurred at 212.99° C.±3° C.

In some embodiments of the present disclosure, the TGA pattern of the crystal form A is as shown in FIG. 3.

The present disclosure provides a crystal form B of the compound of formula (I), wherein the X-ray powder diffraction pattern thereof comprises characteristic diffraction peaks at the following angle 2θ: 11.10±0.2°, 18.00±0.2° and 19.84±0.2°.

In some embodiments of the present disclosure, the X-ray powder diffraction pattern of the crystal form B comprises characteristic diffraction peaks at the following angle 2θ: 9.31±0.2°, 11.10±0.2°, 11.73±0.2°, 13.94±0.2°, 14.77±0.2°, 16.52±0.2°, 18.00±0.2°, and 19.84±0.2°.

In some embodiments of the present disclosure, the XRPD pattern of the crystal form B is as shown in FIG. 4.

In some embodiments of the present disclosure, the analytical data of the XRPD pattern of the crystal form B is as shown in Table 2:

TABLE 2

XRPD diffraction data of the crystal form B of the compound of formula (I)

| No. | 2θ Angle (°) | d-spacing (Å) | Relative intensity (%) |
| --- | --- | --- | --- |
| 1 | 9.307 | 9.4943 | 16.3 |
| 2 | 11.1 | 7.9645 | 71.9 |
| 3 | 11.728 | 7.5395 | 17.7 |
| 4 | 13.94 | 6.3477 | 24.7 |
| 5 | 14.769 | 5.9932 | 48.1 |
| 6 | 16.523 | 5.3608 | 21.8 |
| 7 | 17.449 | 5.0781 | 5.1 |
| 8 | 18.005 | 4.9227 | 61.7 |
| 9 | 18.592 | 4.7684 | 13.1 |
| 10 | 19.836 | 4.4721 | 100 |
| 11 | 20.428 | 4.3439 | 5.3 |
| 12 | 20.804 | 4.2663 | 30.8 |
| 13 | 22.066 | 4.0249 | 29.7 |
| 14 | 22.478 | 3.9522 | 25.3 |
| 15 | 23.466 | 3.788 | 49.2 |
| 16 | 23.679 | 3.7543 | 19.6 |
| 17 | 24.256 | 3.6663 | 12.5 |
| 18 | 24.768 | 3.5917 | 9.3 |
| 19 | 25.955 | 3.43 | 6.4 |
| 20 | 26.897 | 3.312 | 9.4 |
| 21 | 27.31 | 3.2629 | 79 |
| 22 | 27.643 | 3.2243 | 13.2 |
| 23 | 28.007 | 3.1832 | 4.9 |
| 24 | 29.066 | 3.0696 | 8.8 |
| 25 | 30.215 | 2.9555 | 3.3 |
| 26 | 31.41 | 2.8457 | 4.5 |
| 27 | 32.296 | 2.7696 | 3 |
| 28 | 33.74 | 2.6543 | 5.5 |
| 29 | 35.398 | 2.5337 | 5.3 |
| 30 | 35.714 | 2.512 | 6.1 |
| 31 | 38.236 | 2.3519 | 3.2 |

The present disclosure provides a crystal form C of the compound of formula (I), wherein the X-ray powder diffraction pattern thereof comprises characteristic diffraction peaks at the following angle 2θ: 10.19±0.2°, 22.84±0.2°, and 24.39±0.2°.

In some embodiments of the present disclosure, the X-ray powder diffraction pattern of the crystal form C comprises characteristic diffraction peaks at the following angle 2θ: 10.19±0.2°, 11.32±0.2°, 18.73±0.2°, 19.71±0.2°, 22.84±0.2°, 24.39±0.2°, 32.10±0.2°, and 34.02±0.2°.

In some embodiments of the present disclosure, the XRPD pattern of the crystal form C is as shown in FIG. 5.

In some embodiments of the present disclosure, the analytical data of the XRPD pattern of the crystal form C is as shown in Table 3:

TABLE 3

XRPD diffraction data of the crystal form C of the compound of formula (I)

| No. | 2θ Angle (°) | d-spacing (Å) | Relative intensity (%) |
| --- | --- | --- | --- |
| 1 | 10.193 | 8.6707 | 100 |
| 2 | 11.318 | 7.8115 | 6 |
| 3 | 14.668 | 6.034 | 8.7 |
| 4 | 14.945 | 5.9229 | 2.5 |
| 5 | 15.915 | 5.564 | 2.3 |
| 6 | 16.423 | 5.393 | 1.4 |
| 7 | 16.978 | 5.218 | 1.8 |
| 8 | 18.734 | 4.7327 | 6.6 |
| 9 | 19.714 | 4.4995 | 2 |
| 10 | 20.429 | 4.3438 | 15.3 |
| 11 | 20.682 | 4.2912 | 6.2 |
| 12 | 21.083 | 4.2104 | 3 |
| 13 | 22.839 | 3.8905 | 11.3 |
| 14 | 24.39 | 3.6465 | 48.7 |
| 15 | 24.867 | 3.5776 | 2.5 |
| 16 | 27.312 | 3.2627 | 5.2 |
| 17 | 27.865 | 3.1992 | 4.3 |
| 18 | 29.402 | 3.0352 | 3.9 |
| 19 | 29.617 | 3.0138 | 4.6 |
| 20 | 32.104 | 2.7858 | 2.9 |
| 21 | 34.016 | 2.6334 | 5.9 |

The present disclosure provides a crystal form D of the compound of formula (I), wherein the X-ray powder diffraction pattern thereof comprises characteristic diffraction peaks at the following angle 2θ: 8.04±0.2°, 11.55±0.2°, and 24.06±0.2°.

In some embodiments of the present disclosure, the X-ray powder diffraction pattern of the crystal form D comprises characteristic diffraction peaks at the following angle 2θ: 8.04±0.2°, 11.55±0.2°, 14.92±0.2°, 15.46±0.2°, 18.04±0.2°, 19.03±0.2°, 22.52±0.2°, and 24.06±0.2°.

In some embodiments of the present disclosure, the XRPD pattern of the crystal form D is as shown in FIG. 6.

In some embodiments of the present disclosure, the analytical data of the XRPD pattern of the crystal form D is as shown in Table 4:

TABLE 4

XRPD diffraction data of the crystal form D of the compound of formula (I)

| No. | 2θ Angle (°) | d-spacing (Å) | Relative intensity (%) |
| --- | --- | --- | --- |
| 1 | 8.044 | 10.9818 | 26.5 |
| 2 | 11.553 | 7.653 | 41.3 |
| 3 | 11.947 | 7.4019 | 4.4 |
| 4 | 13.13 | 6.7372 | 16.2 |
| 5 | 13.447 | 6.5794 | 5.1 |
| 6 | 13.661 | 6.4768 | 4 |
| 7 | 14.513 | 6.0982 | 12.7 |
| 8 | 14.924 | 5.9314 | 21.7 |
| 9 | 15.458 | 5.7276 | 19.8 |
| 10 | 16.185 | 5.4717 | 6.3 |
| 11 | 16.428 | 5.3914 | 9.5 |
| 12 | 17.254 | 5.1353 | 15.9 |
| 13 | 17.507 | 5.0616 | 9.7 |
| 14 | 18.043 | 4.9124 | 25 |
| 15 | 19.029 | 4.66 | 59.2 |
| 16 | 19.556 | 4.5356 | 9.4 |
| 17 | 19.799 | 4.4805 | 18.3 |
| 18 | 20.154 | 4.4024 | 12.1 |
| 19 | 20.487 | 4.3315 | 4 |
| 20 | 20.74 | 4.2792 | 5.9 |
| 21 | 21.707 | 4.0907 | 8.3 |
| 22 | 21.889 | 4.0572 | 6 |
| 23 | 22.519 | 3.945 | 32.9 |

TABLE 4-continued

XRPD diffraction data of the crystal
form D of the compound of formula (I)

| No. | 2θ Angle (°) | d-spacing (Å) | Relative intensity (%) |
|---|---|---|---|
| 24 | 23.034 | 3.8579 | 4.1 |
| 25 | 23.341 | 3.8079 | 4.1 |
| 26 | 23.784 | 3.7381 | 9.8 |
| 27 | 24.056 | 3.6963 | 100 |
| 28 | 24.669 | 3.6058 | 22.8 |
| 29 | 25.458 | 3.4959 | 4.8 |
| 30 | 26.047 | 3.4181 | 6.4 |
| 31 | 26.323 | 3.383 | 3.6 |
| 32 | 27.762 | 3.2107 | 7.5 |
| 33 | 28.276 | 3.1536 | 3.7 |
| 34 | 29.244 | 3.0513 | 6.4 |
| 35 | 29.54 | 3.0214 | 8.4 |
| 36 | 30.701 | 2.9098 | 5.4 |
| 37 | 36.505 | 2.4593 | 2.9 |

The present disclosure provides a crystal form E of the compound of formula (I), wherein the X-ray powder diffraction pattern thereof comprises characteristic diffraction peaks at the following angle 2θ: 5.30±0.2°, 15.93±0.2°, and 18.79±0.2°.

In some embodiments of the present disclosure, the X-ray powder diffraction pattern of the crystal form E comprises characteristic diffraction peaks at the following angle 2θ: 5.30±0.2°, 10.62±0.2°, 11.16±0.2°, 14.47±0.2°, 15.93±0.2°, 17.33±0.220, 18.79±0.2°, and 32.16±0.2°.

In some embodiments of the present disclosure, the XRPD pattern of the crystal form E is as shown in FIG. 7.

In some embodiments of the present disclosure, the analytical data of the XRPD pattern of the crystal form E is as shown in Table 5:

TABLE 5

XRPD diffraction data of the crystal
form E of the compound of formula (I)

| No. | 2θ Angle (°) | d-spacing (Å) | Relative intensity (%) |
|---|---|---|---|
| 1 | 5.302 | 16.6538 | 31.3 |
| 2 | 8.793 | 10.0484 | 4.4 |
| 3 | 9.463 | 9.3386 | 3.6 |
| 4 | 10.625 | 8.3195 | 48 |
| 5 | 11.16 | 7.9221 | 8.3 |
| 6 | 14.472 | 6.1155 | 18.3 |
| 7 | 15.931 | 5.5585 | 100 |
| 8 | 16.638 | 5.3239 | 3.6 |
| 9 | 17.331 | 5.1125 | 8.5 |
| 10 | 18.791 | 4.7185 | 35.5 |
| 11 | 20.388 | 4.3524 | 6.5 |
| 12 | 20.981 | 4.2306 | 31.3 |
| 13 | 21.238 | 4.18 | 71.1 |
| 14 | 21.786 | 4.0761 | 4.8 |
| 15 | 22.403 | 3.9652 | 9.5 |
| 16 | 23.704 | 3.7504 | 11.4 |
| 17 | 24.036 | 3.6993 | 9.8 |
| 18 | 25.183 | 3.5334 | 7.9 |
| 19 | 26.265 | 3.3902 | 15.9 |
| 20 | 26.622 | 3.3456 | 14.9 |
| 21 | 27.192 | 3.2768 | 5.5 |
| 22 | 27.965 | 3.1879 | 3.6 |
| 23 | 32.162 | 2.7808 | 9.5 |

The present disclosure provides a compound of formula (II),

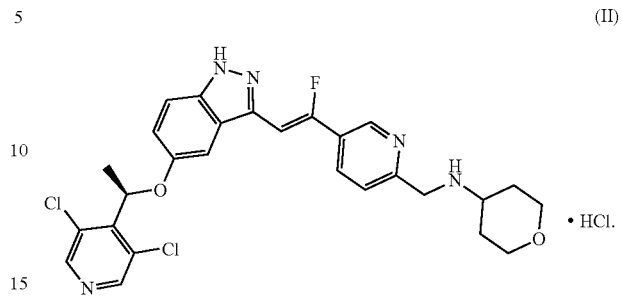

(II)

The present disclosure provides a crystal form F of the compound of formula (II), wherein the X-ray powder diffraction pattern thereof comprises characteristic diffraction peaks at the following angle 2θ: 4.98±0.2°, 7.49±0.2°, and 19.18±0.2°.

In some embodiments of the present disclosure, the X-ray powder diffraction pattern of the crystal form F comprises characteristic diffraction peaks at the following angle 2θ: 4.98±0.2°, 7.49±0.2°, 9.82±0.2°, 12.15±0.2°, 17.27±0.2°, 19.18±0.2°, 20.10±0.2°, and 21.79±0.2°.

In some embodiments of the present disclosure, the XRPD pattern of the crystal form F is as shown in FIG. 8.

In some embodiments of the present disclosure, the analytical data of the XRPD pattern of the crystal form F is as shown in Table 6:

TABLE 6

XRPD diffraction data of the crystal form
F of the compound of formula (II)

| No. | 2θ Angle (°) | d-spacing (Å) | Relative intensity (%) |
|---|---|---|---|
| 1 | 4.985 | 17.7111 | 25.9 |
| 2 | 7.492 | 11.79 | 20.8 |
| 3 | 9.816 | 9.0029 | 27.8 |
| 4 | 12.149 | 7.2793 | 13.3 |
| 5 | 14.924 | 5.9311 | 33.3 |
| 6 | 15.319 | 5.7793 | 39.2 |
| 7 | 17.273 | 5.1294 | 28.4 |
| 8 | 19.185 | 4.6225 | 100 |
| 9 | 19.615 | 4.522 | 25.7 |
| 10 | 20.101 | 4.4138 | 17.8 |
| 11 | 20.805 | 4.266 | 22.2 |
| 12 | 21.1 | 4.2071 | 24.1 |
| 13 | 21.79 | 4.0754 | 37.8 |
| 14 | 23.19 | 3.8324 | 60.4 |
| 15 | 23.504 | 3.7819 | 31.6 |
| 16 | 25.081 | 3.5476 | 14.9 |
| 17 | 25.733 | 3.4592 | 40.6 |
| 18 | 26.149 | 3.4051 | 64.9 |
| 19 | 27.289 | 3.2653 | 46.5 |
| 20 | 28.532 | 3.1258 | 17.3 |
| 21 | 29.418 | 3.0337 | 18.6 |
| 22 | 32.379 | 2.7627 | 15.7 |
| 23 | 35.38 | 2.5349 | 16.1 |

In some embodiments of the present disclosure, the differential scanning calorimetry curve of the crystal form F has an onset point of an endothermic peak at 172.07° C.±3° C. and 277.05° C.±3° C. respectively, and has an onset point of an exothermic peak at 284.37° C.±3° C.

In some embodiments of the present disclosure, the DSC pattern of the crystal form F is as shown in FIG. 9.

In some embodiments of the present disclosure, the thermogravimetric analysis curve of the crystal form F has a weight loss of 3.578% occurred at 153.13° C.±3° C.

In some embodiments of the present disclosure, the TGA pattern of the crystal form F is as shown in FIG. 10.

The present disclosure provides a crystal form G of the compound of formula (II), wherein the X-ray powder diffraction pattern thereof comprises characteristic diffraction peaks at the following angle 2θ: 7.39±0.2°, 19.07±0.2°, and 20.04±0.2°.

In some embodiments of the present disclosure, the X-ray powder diffraction pattern of the crystal form G comprises characteristic diffraction peaks at the following angle 2θ: 7.39±0.2°, 19.07±0.2°, 20.04±0.2°, 21.05±0.2°, 21.76±0.2°, 25.64±0.2°, 26.23±0.2°, and 27.16±0.2°.

In some embodiments of the present disclosure, the XRPD pattern of the crystal form G is as shown in FIG. 11.

In some embodiments of the present disclosure, the analytical data of the XRPD pattern of the crystal form G is as shown in Table 7:

TABLE 7

XRPD diffraction data of the crystal form G of the compound of formula (II)

| No. | 2θ Angle (°) | d-spacing (Å) | Relative intensity (%) |
|---|---|---|---|
| 1 | 7.393 | 11.948 | 9.6 |
| 2 | 12.087 | 7.3161 | 14.3 |
| 3 | 12.42 | 7.1208 | 6.8 |
| 4 | 13.23 | 6.6868 | 3.7 |
| 5 | 13.475 | 6.5656 | 4.3 |
| 6 | 15.206 | 5.822 | 33.5 |
| 7 | 15.576 | 5.6845 | 2.9 |
| 8 | 17.213 | 5.1473 | 29.9 |
| 9 | 17.495 | 5.0651 | 13.5 |
| 10 | 17.767 | 4.9881 | 9.7 |
| 11 | 18.198 | 4.8708 | 4.6 |
| 12 | 18.559 | 4.7768 | 2.7 |
| 13 | 19.073 | 4.6494 | 100 |
| 14 | 20.035 | 4.4281 | 20.4 |
| 15 | 21.046 | 4.2177 | 15.1 |
| 16 | 21.755 | 4.0818 | 37.6 |
| 17 | 22.902 | 3.8799 | 12.6 |
| 18 | 23.134 | 3.8416 | 34 |
| 19 | 23.294 | 3.8155 | 24.5 |
| 20 | 23.433 | 3.7932 | 21 |
| 21 | 24.003 | 3.7043 | 2.6 |
| 22 | 24.282 | 3.6624 | 8.3 |
| 23 | 24.66 | 3.6072 | 6.1 |
| 24 | 24.957 | 3.5649 | 10.6 |
| 25 | 25.308 | 3.5163 | 11.4 |
| 26 | 25.643 | 3.4711 | 44.6 |
| 27 | 26.233 | 3.3943 | 14.7 |
| 28 | 27.157 | 3.2809 | 56.1 |
| 29 | 28.424 | 3.1375 | 10.2 |
| 30 | 28.583 | 3.1204 | 8.5 |
| 31 | 29.309 | 3.0447 | 5.3 |
| 32 | 29.55 | 3.0204 | 4 |
| 33 | 30.654 | 2.9141 | 7 |
| 34 | 31.106 | 2.8728 | 5.4 |
| 35 | 31.461 | 2.8412 | 2.6 |
| 36 | 31.854 | 2.807 | 3.4 |
| 37 | 32.307 | 2.7687 | 7.5 |
| 38 | 33.297 | 2.6886 | 5.4 |
| 39 | 33.731 | 2.655 | 3.5 |
| 40 | 34.836 | 2.5733 | 3.1 |
| 41 | 35.403 | 2.5333 | 6.6 |
| 42 | 36.672 | 2.4485 | 2.2 |
| 43 | 37.14 | 2.4187 | 3.9 |
| 44 | 37.755 | 2.3807 | 3.1 |

In some embodiments of the present disclosure, the differential scanning calorimetry curve of the crystal form G has an onset point of an endothermic peak at 278.70° C.±3° C., and has an onset point of an exothermic peak at 285.46° C.±3° C.

In some embodiments of the present disclosure, the DSC pattern of the crystal form G is as shown in FIG. 12.

In some embodiments of the present disclosure, the thermogravimetric analysis curve of the crystal form G has a weight loss of 3.870% occurred at 120° C. 3° C. and a weight loss of 1.170% occurred at 221.76° C.±3° C.

In some embodiments of the present disclosure, the TGA pattern of the crystal form G is as shown in FIG. 13.

The present disclosure provides a crystal form H of the compound of formula (II), wherein the X-ray powder diffraction pattern thereof comprises characteristic diffraction peaks at the following angle 2θ: 4.95±0.2°, 7.30±0.2°, and 19.01±0.2°.

In some embodiments of the present disclosure, the X-ray powder diffraction pattern of the crystal form H comprises characteristic diffraction peaks at the following angle 2θ: 4.95±0.2°, 7.30±0.2°, 11.99±0.2°, 14.36±0.2°, 16.66±0.2°, 18.26±0.2°, 19.01±0.2°, and 21.49±0.2°.

In some embodiments of the present disclosure, the XRPD pattern of the crystal form H is as shown in FIG. 14.

In some embodiments of the present disclosure, the analytical data of the XRPD pattern of the crystal form H is as shown in Table 8:

TABLE 8

XRPD diffraction data of the crystal form H of the compound of formula (II)

| No. | 2θ Angle (°) | d-spacing (Å) | Relative intensity (%) |
|---|---|---|---|
| 1 | 4.949 | 17.8408 | 17.2 |
| 2 | 7.295 | 12.1076 | 12 |
| 3 | 8.576 | 10.3015 | 6.4 |
| 4 | 11.99 | 7.3753 | 9.3 |
| 5 | 14.361 | 6.1624 | 10.1 |
| 6 | 14.987 | 5.9064 | 13.2 |
| 7 | 15.163 | 5.8382 | 20.1 |
| 8 | 16.028 | 5.5252 | 6.3 |
| 9 | 16.661 | 5.3167 | 16.7 |
| 10 | 17.15 | 5.166 | 20 |
| 11 | 17.428 | 5.0843 | 9.8 |
| 12 | 17.706 | 5.005 | 9.4 |
| 13 | 18.257 | 4.8552 | 31.1 |
| 14 | 19.01 | 4.6647 | 100 |
| 15 | 19.972 | 4.4419 | 12.4 |
| 16 | 20.19 | 4.3945 | 13.6 |
| 17 | 20.693 | 4.2888 | 6.9 |
| 18 | 20.981 | 4.2305 | 10.9 |
| 19 | 21.492 | 4.1312 | 41.6 |
| 20 | 21.689 | 4.094 | 25.7 |
| 21 | 22.014 | 4.0343 | 9.9 |
| 22 | 22.876 | 3.8843 | 3.9 |
| 23 | 23.055 | 3.8546 | 20.5 |
| 24 | 23.37 | 3.8033 | 17.3 |
| 25 | 24.315 | 3.6575 | 30.5 |
| 26 | 24.769 | 3.5916 | 15.7 |
| 27 | 25.359 | 3.5093 | 78.8 |
| 28 | 25.576 | 3.48 | 47.5 |
| 29 | 26.17 | 3.4024 | 16.8 |
| 30 | 27.093 | 3.2885 | 46.1 |
| 31 | 28.358 | 3.1446 | 10.1 |
| 32 | 29.008 | 3.0756 | 5.8 |
| 33 | 29.638 | 3.0116 | 20.3 |
| 34 | 29.893 | 2.9865 | 5.2 |
| 35 | 30.58 | 2.921 | 3.9 |
| 36 | 31.158 | 2.8681 | 3.5 |
| 37 | 31.394 | 2.8471 | 3.5 |
| 38 | 32.223 | 2.7757 | 6.8 |
| 39 | 33.288 | 2.6893 | 5 |
| 40 | 33.426 | 2.6785 | 7.6 |

TABLE 8-continued

XRPD diffraction data of the crystal form
H of the compound of formula (II)

| No. | 2θ Angle (°) | d-spacing (Å) | Relative intensity (%) |
|---|---|---|---|
| 41 | 33.726 | 2.6554 | 4.5 |
| 42 | 34.446 | 2.6015 | 3.8 |
| 43 | 34.824 | 2.5741 | 3.9 |
| 44 | 35.142 | 2.5516 | 7.9 |
| 45 | 36.448 | 2.463 | 5.5 |
| 46 | 37.733 | 2.3821 | 2.8 |

In some embodiments of the present disclosure, the differential scanning calorimetry curve of the crystal form H has an onset point of an endothermic peak at 172.97° C.±3° C. and 277.33° C.±3° C. respectively, and has an onset point of an exothermic peak at 283.38° C.±3° C.

In some embodiments of the present disclosure, the DSC pattern of the crystal form H is as shown in FIG. 15.

In some embodiments of the present disclosure, the thermogravimetric analysis curve of the crystal form H has a weight loss of 0.8819% occurred at 120° C. 3° C. and a weight loss of 2.892% occurred at 206.30° C.±3° C.

In some embodiments of the present disclosure, the TGA pattern of the crystal form H is as shown in FIG. 16.

The present disclosure provides a compound of formula (III),

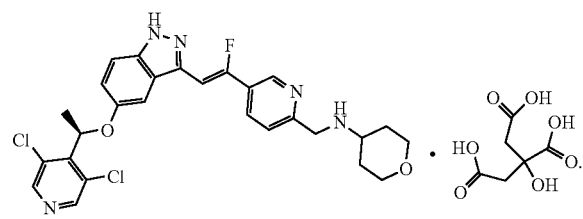

(III)

The present disclosure provides s crystal form I of the compound of formula (III), wherein the X-ray powder diffraction pattern thereof comprises characteristic diffraction peaks at the following angle 2θ: 6.73±0.2°, 11.66±0.2°, and 19.51±0.2°.

In some embodiments of the present disclosure, the X-ray powder diffraction pattern of the crystal form I comprises characteristic diffraction peaks at the following angle 2θ: 6.73±0.2°, 11.66±0.2°, 14.28±0.2°, 14.99±0.2°, 16.39±0.2°, 19.51±0.2°, 23.34±0.2°, and 25.61±0.2°.

In some embodiments of the present disclosure, the XRPD pattern of the crystal form I is as shown in FIG. 17.

In some embodiments of the present disclosure, the analytical data of the XRPD pattern of the crystal form I is as shown in Table 9:

TABLE 9

XRPD diffraction data of the crystal form
I of the compound of formula (II)

| No. | 2θ Angle (°) | d-spacing (Å) | Relative intensity (%) |
|---|---|---|---|
| 1 | 6.727 | 13.128 | 9.7 |
| 2 | 9.96 | 8.8732 | 5.8 |
| 3 | 11.656 | 7.5858 | 19.9 |
| 4 | 12.133 | 7.2887 | 5.6 |
| 5 | 13.293 | 6.6551 | 6.4 |
| 6 | 13.833 | 6.3963 | 6.8 |
| 7 | 14.283 | 6.1961 | 8.8 |
| 8 | 14.993 | 5.9039 | 13.4 |
| 9 | 16.394 | 5.4027 | 10 |
| 10 | 17.641 | 5.0233 | 9.7 |
| 11 | 17.975 | 4.9307 | 13 |
| 12 | 18.807 | 4.7145 | 8.7 |
| 13 | 19.514 | 4.5452 | 100 |
| 14 | 19.889 | 4.4604 | 46.3 |
| 15 | 20.996 | 4.2277 | 18.8 |
| 16 | 21.612 | 4.1085 | 7.7 |
| 17 | 22.197 | 4.0016 | 22.3 |
| 18 | 23.343 | 3.8075 | 56.7 |
| 19 | 24.297 | 3.6602 | 6.2 |
| 20 | 25.614 | 3.4749 | 38.2 |
| 21 | 26.662 | 3.3406 | 7.7 |
| 22 | 27.745 | 3.2127 | 16.2 |
| 23 | 28.71 | 3.1068 | 4.3 |
| 24 | 30.448 | 2.9334 | 10 |
| 25 | 36.059 | 2.4887 | 7 |

In some embodiments of the present disclosure, the differential scanning calorimetry curve of the crystal form I has an onset point of an endothermic peak at 32.94° C.±3° C. and 204.62° C.±3° C. respectively.

In some embodiments of the present disclosure, the DSC pattern of the crystal form I is as shown in FIG. 18.

In some embodiments of the present disclosure, the thermogravimetric analysis curve of the crystal form I has a weight loss of 0.8601% occurred at 85.39° C.±3° C. and a weight loss of 2.264% occurred at 184.93° C.±3° C.

In some embodiments of the present disclosure, the TGA pattern of the crystal form I is as shown in FIG. 19.

The present disclosure provides a compound of formula (IV),

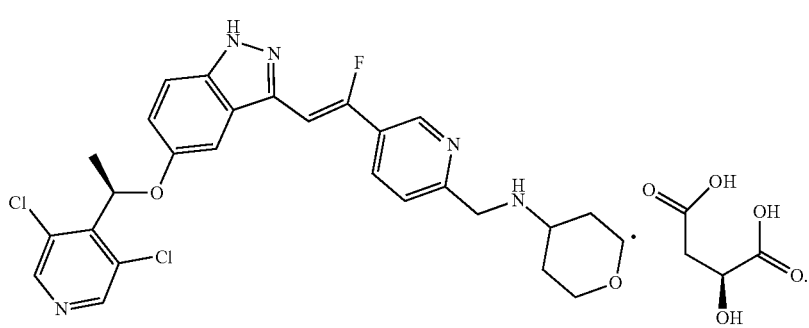

(IV)

The present disclosure provides a crystal form J of the compound of formula (IV), wherein the X-ray powder diffraction pattern thereof comprises characteristic diffraction peaks at the following angle 2θ: 4.99±0.2°, 11.32±0.2°, and 19.95±0.2°.

In some embodiments of the present disclosure, the X-ray powder diffraction pattern of the crystal form J comprises characteristic diffraction peaks at the following angle 2θ: 4.99±0.2°, 6.90±0.2°, 9.9±0.2°, 10.73±0.2°, 11.32±0.2°, 14.41±0.2°, 16.73±0.2°, and 19.95±0.2°.

In some embodiments of the present disclosure, the XRPD pattern of the crystal form J is as shown in FIG. 21.

In some embodiments of the present disclosure, the analytical data of the XRPD pattern of the crystal form J is as shown in Table 10:

TABLE 10

XRPD diffraction data of the crystal form J of the compound of formula (IV)

| No. | 2θ Angle (°) | d-spacing (Å) | Relative intensity (%) |
|---|---|---|---|
| 1 | 4.987 | 17.7057 | 23 |
| 2 | 6.905 | 12.791 | 12.5 |
| 3 | 9.9 | 8.9268 | 15.4 |
| 4 | 10.732 | 8.237 | 24 |
| 5 | 11.323 | 7.8079 | 57.5 |
| 6 | 11.937 | 7.4077 | 10.1 |
| 7 | 13.848 | 6.3894 | 11.7 |
| 8 | 14.406 | 6.1432 | 42 |
| 9 | 14.839 | 5.965 | 32.3 |
| 10 | 15.072 | 5.8732 | 17 |
| 11 | 16.729 | 5.295 | 21.8 |
| 12 | 17.82 | 4.9734 | 18.9 |
| 13 | 18.328 | 4.8365 | 39.4 |
| 14 | 19.036 | 4.6583 | 14.4 |
| 15 | 19.694 | 4.5042 | 54.8 |
| 16 | 19.948 | 4.4474 | 100 |
| 17 | 20.699 | 4.2877 | 22.5 |
| 18 | 20.94 | 4.2388 | 35.7 |
| 19 | 21.486 | 4.1322 | 18 |
| 20 | 21.939 | 4.0479 | 21.7 |
| 21 | 23.484 | 3.785 | 56.2 |
| 22 | 23.755 | 3.7424 | 19.7 |
| 23 | 25.494 | 3.4911 | 10.3 |
| 24 | 25.909 | 3.436 | 48.4 |
| 25 | 27.763 | 3.2106 | 15.2 |
| 26 | 28.158 | 3.1665 | 15.6 |
| 27 | 29.044 | 3.0719 | 9 |
| 28 | 30.864 | 2.8947 | 6.8 |
| 29 | 32.697 | 2.7365 | 8.4 |
| 30 | 35.52 | 2.5252 | 4.8 |
| 31 | 36.078 | 2.4874 | 7.7 |

In some embodiments of the present disclosure, the differential scanning calorimetry curve of the crystal form J has an onset point of an endothermic peak at 33.34° C.±3° C. and 194.84° C.±3° C. respectively.

In some embodiments of the present disclosure, the DSC pattern of the crystal form J is as shown in FIG. 22.

In some embodiments of the present disclosure, the thermogravimetric analysis curve of the crystal form J has a weight loss of 1.357% occurred at 120° C.±3° C. and a weight loss of 0.8330% occurred at 177.11° C.±3° C.

In some embodiments of the present disclosure, the TGA pattern of the crystal form J is as shown in FIG. 23.

The present disclosure provides a preparation method of the crystal form of a compound of formula (I), (II), (III) or (IV), which comprises adding the compound of formula (I), (II), (III) or (IV) to a solvent respectively; and heating and stirring, or recrystallizing.

In some embodiments of the present disclosure, the solvent is selected from methanol, ethanol, acetone, tetrahydrofuran, ethyl acetate, ethyl acetate-ethanol, isopropanol, or ethanol-water.

In some embodiments of the present disclosure, the stirring is performed at a temperature of 35° C. to 45° C.

In some embodiments of the present disclosure, the slurrying time is 12 hours to 36 hours.

In some embodiments of the present disclosure, the weight ratio of the compound to the solvent is 1:10 to 1:15.

The present disclosure provides a preparation method of the crystal form G of the compound of formula (II), which comprises adding the compound of formula (I) into ethanol, adding hydrochloric acid/ethyl acetate dropwise to the reaction bottle, heating and stirring, cooling to room temperature, and filtering.

In some embodiments of the present disclosure, the heating and stirring of the crystal form G of the compound of formula (II) is performed at a temperature of 85° C. to 95° C.

In some embodiments of the present disclosure, a use of the compound or the crystal form thereof in the manufacture of a medicament for treating tyrosine kinase inhibitor related diseases is provided.

DEFINITIONS AND EXPLANATIONS

Unless otherwise indicated, the following terms and phrases used herein are intended to have the following meanings. A specific term or phrase should not be considered indefinite or unclear in the absence of a particular definition, but should be understood in the ordinary sense. When a trade name appears herein, it is intended to refer to its corresponding commodity or active ingredient thereof.

The intermediate compounds of the present disclosure can be prepared by various synthetic methods known to those skilled in the art, including the embodiments described below, the embodiments formed by combining the embodiments described below with other chemical synthesis methods, and equivalent alternatives well-known for those skilled in the art. Preferred embodiments include, but are not limited to, the embodiments of the present disclosure.

The chemical reactions of the embodiments of the present disclosure are carried out in a suitable solvent, and the solvent should be suitable for the chemical change, and the reagents and materials required therefor of the present disclosure. In order to obtain the compounds of the present disclosure, it is sometimes necessary for those skilled in the art to modify or select the synthetic steps or reaction schemes based on the existing embodiments.

The present invention will be specifically described below by way of embodiments, but the scope of the present invention is not limited thereto.

All solvents used in the present disclosure are commercially available and can be directly used without further purification.

The present disclosure employs the following abbreviations: r.t. stands for room temperature; THF stands for tetrahydrofuran; NMP stands for N-methylpyrrolidone; $MeSO_3H$ stands for methanesulfonic acid; DME stands for dimethoxyethane; DCM stands for dichloromethane; Xphos stands for 2-dicyclohexylphospho-2',4',6'-triisopropylbiphenyl; EtOAc stands for ethyl acetate; MeOH stands for methanol; acetone stands for propanone; 2-Me-THF stands for 2-methyltetrahydrofuran; IPA stands for isopropanol; m-CPBA stands for 3-chloroperoxybenzoic acid; Pd(dppf)$Cl_2$ stands for [1,1'-bis(diphenylphosphino)ferrocene]palladium dichloride; DIEA stands for NN-diisopropylethylamine; DMSO stands for dimethyl sulfoxide; HEPES stands for 2-[4-(2-hydroxyethyl)piperazin-1-yl]ethanesulfonic acid; EGTA stands for ethylene glycol bis(2-aminoethyl ether) tetraacetic acid; THP stands for tetrahydropyranyl.

Compounds are named manually or by ChemDraw® software, and the commercially available compounds use their vendor directory names.

X-RAY POWDER DIFFRACTOMETER (XRPD) METHOD OF THE PRESENT DISCLOSURE

Instrument model: Bruker D8 advance X-ray diffractometer

Detection method: about 10-20 mg of the sample was used for XRPD detection.

The detailed XRPD parameters were as follows:
X-ray tube: Cu, kα, (λ=1.54056 Å).
X-ray tube voltage: 40 kV, X-ray tube current: 40 mA
Divergence slit: 0.60 mm
Detector slit: 10.50 mm
Anti-scattering slit: 7.10 mm
Scanning range: 4-40 deg
Step size: 0.02 deg
Step time: 0.12 seconds
Rotation speed of sample tray: 15 rpm

DIFFERENTIAL SCANNING CALORIMETER (DSC) METHOD OF THE PRESENT DISCLOSURE

Instrument Model: TA Q2000 differential scanning calorimeter

Detection method: samples (about 1 mg) were placed in a DSC aluminum crucible for detection, and heated from 30° C. (room temperature) to 300° C. (or 350° C.) with a heating rate of 10° C./min under the condition of 50 mL/min $N_2$.

THERMAL GRAVIMETRIC ANALYZER (TGA) METHOD OF THE PRESENT DISCLOSURE

Instrument Model: TA Q5000IR thermal gravimetric analyzer

Detection method: samples (2 mg to 5 mg) were placed in a TGA platinum crucible for detection, and heated with a heating rate of 10° C./min under the condition of 25 mL/min $N_2$ from room temperature to 300° C. or till 20% weight thereof were lost.

DYNAMIC VAPOR SORPTION (DVS) OF THE PRESENT DISCLOSURE

Instrument model: SMS DVS Advantage dynamic vapor sorption analyzer

Detection conditions: samples (10 mg to 15 mg) were placed in a DVS sample tray for detection.

The detailed DVS parameters are as follows:
Temperature: 25° C.
Balance: dm/dt=0.01%/min (shortest: 10 min, longest: 180 min)
Drying: 120 minutes at 0% RH
RH (%) gradient for testing: 10%
RH (%) range for gradient testing: 0%-90%-0%

The hygroscopicity was evaluated using the following scales:

| Scales for hygroscopicity | Hygroscopic weight gain* |
|---|---|
| Deliquescence | Absorbing sufficient water to form liquid |
| High hygroscopicity | Δ W % ≥ 15% |
| Medium hygroscopicity | 15% > Δ W % ≥ 2% |
| Low hygroscopicity | 2% > Δ W % ≥ 0.2% |
| No or almost no hygroscopicity | ΔW % < 0.2% |

*Hygroscopic weight gain at 25 ± 1° C. and 80 ± 2% RH

HIGH PERFORMANCE LIQUID CHROMATOGRAPH (HPLC)

The chromatograph conditions for the analysis method of the compound contents is as shown in Table 11.

TABLE 11

| HPLC analysis method for detecting content | |
|---|---|
| Instrument | Agilent 1200 high performance liquid chromatograph (PDS-PF-HPLC-02 or PDS-PF-HPLC-01) |
| Column | Ascentis Express C18 (4.6 × 150 mm, 2.7 μm)(PDS-HPLC-94) |
| Mobile phase A | 0.1% Phosphoric acid aqueous solution |
| Mobile phase B | 100% Acetonitrile |
| Flow rate | 1 mL/min |
| Injection volume | 10 μL |
| Detection wavelength | 280 nm |
| Column temperature | 40° C. |
| Diluent | N,N-dimethylformamide:acetonitrile 50/50(v/v) or acetonitrile:water 1/1 (v/v) |

| Gradient elution procedure | Time (min) | Mobile phase A (%) | Mobile phase B (%) |
|---|---|---|---|
| | 0.00 | 90 | 10 |
| | 13.00 | 5 | 95 |
| | 15.00 | 5 | 95 |
| | 15.01 | 90 | 10 |
| | 18.00 | 90 | 10 |

TECHNICAL EFFECT

The compounds of the present disclosure have excellent in vitro FGFR1 kinase inhibitory activity and SNU-16 cell inhibitory activity, and can be used as a small molecule tyrosine kinase inhibitor; they can inhibit cell proliferation and angiogenesis, have excellent antitumor activity, and have excellent effect in treating various mammals (including humans).

The solubility data of the salts of the present disclosure show that the hydrochloride has the highest solubility in the aqueous phase, and the three salts have similar solubility in simulated intestinal fluid and simulated gastric fluid; and the free base has good solubility in the three biological vehicle, but is extremely difficult to dissolve in water. Crystal forms G, I, and J have excellent thermal stability and stability under accelerated conditions, generate slight impurities under light irradiation conditions, and exhibit good stability under dark condition.

DETAILED DESCRIPTION OF THE PREFERRED EMBODIMENT

Figure 1:
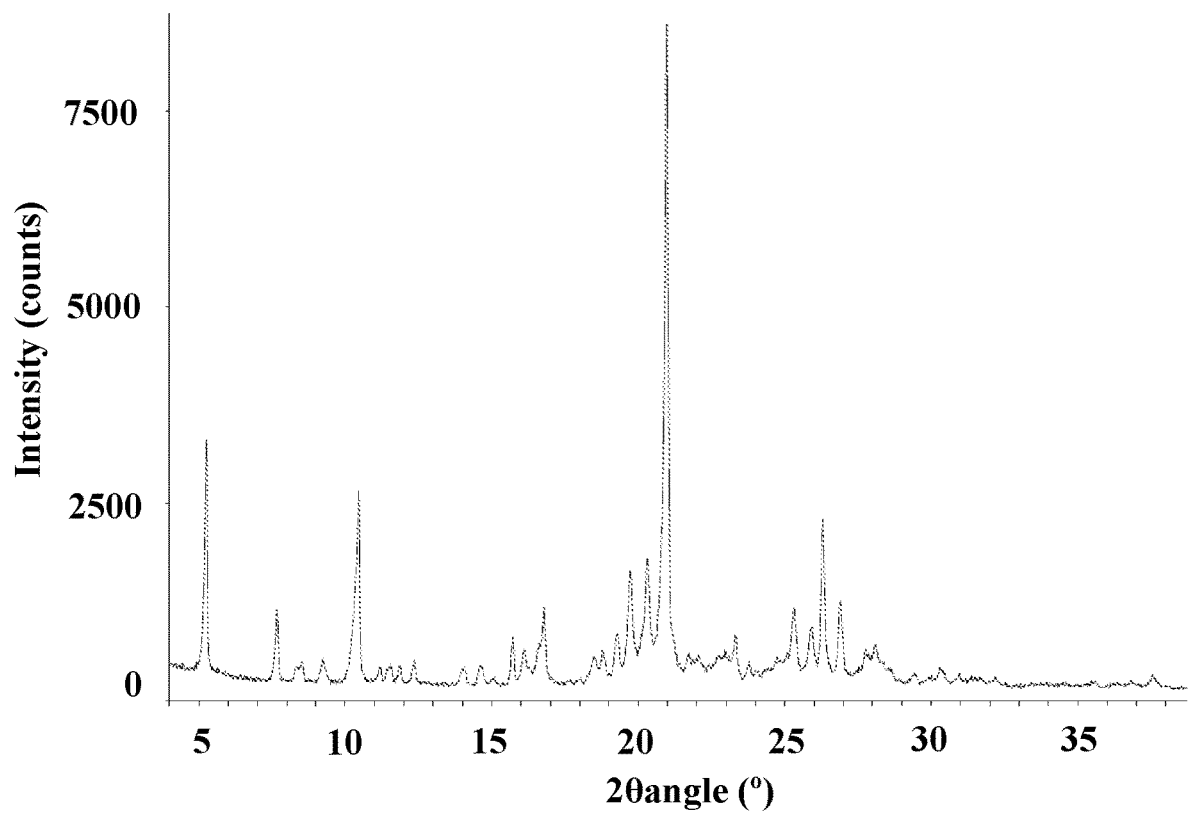
FIG. 1: the XRPD pattern measured by Cu-Kα radiation of the crystal form A of the compound of formula (I).
Figure 2:
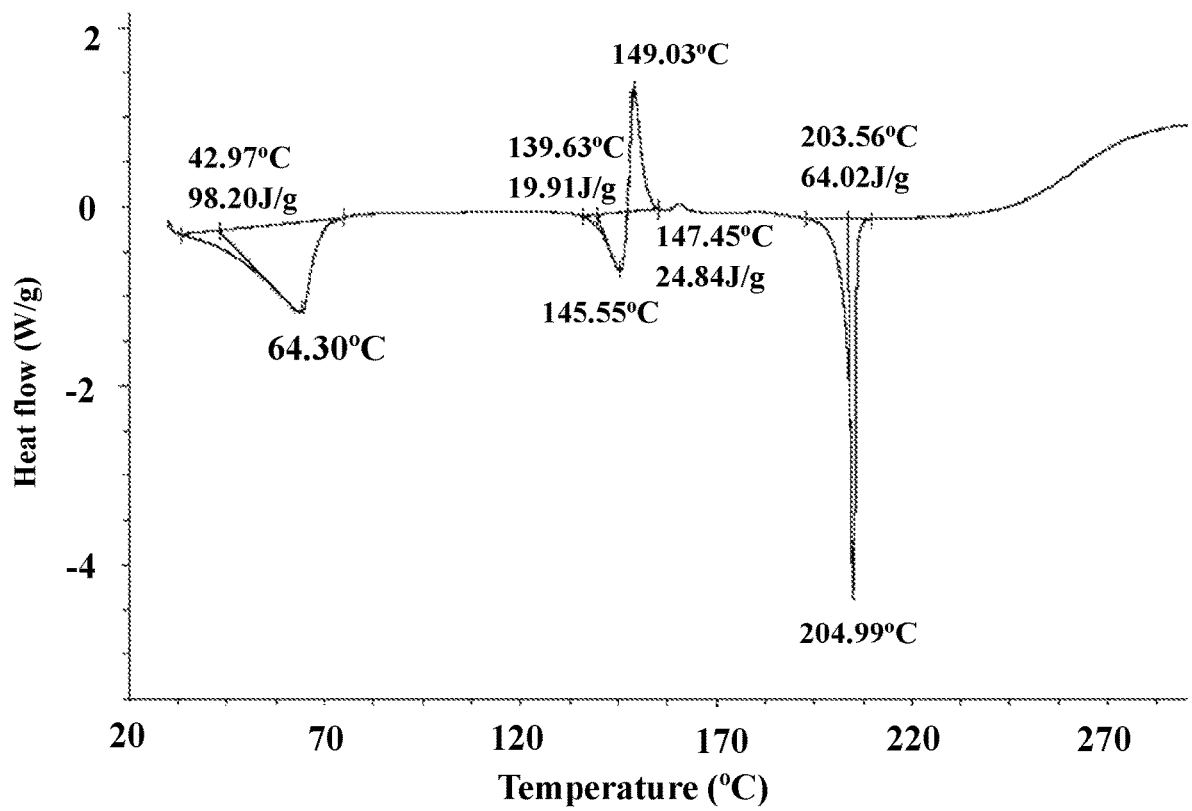
FIG. 2: the DSC pattern of the crystal form A of the compound of formula (I)
Figure 3:
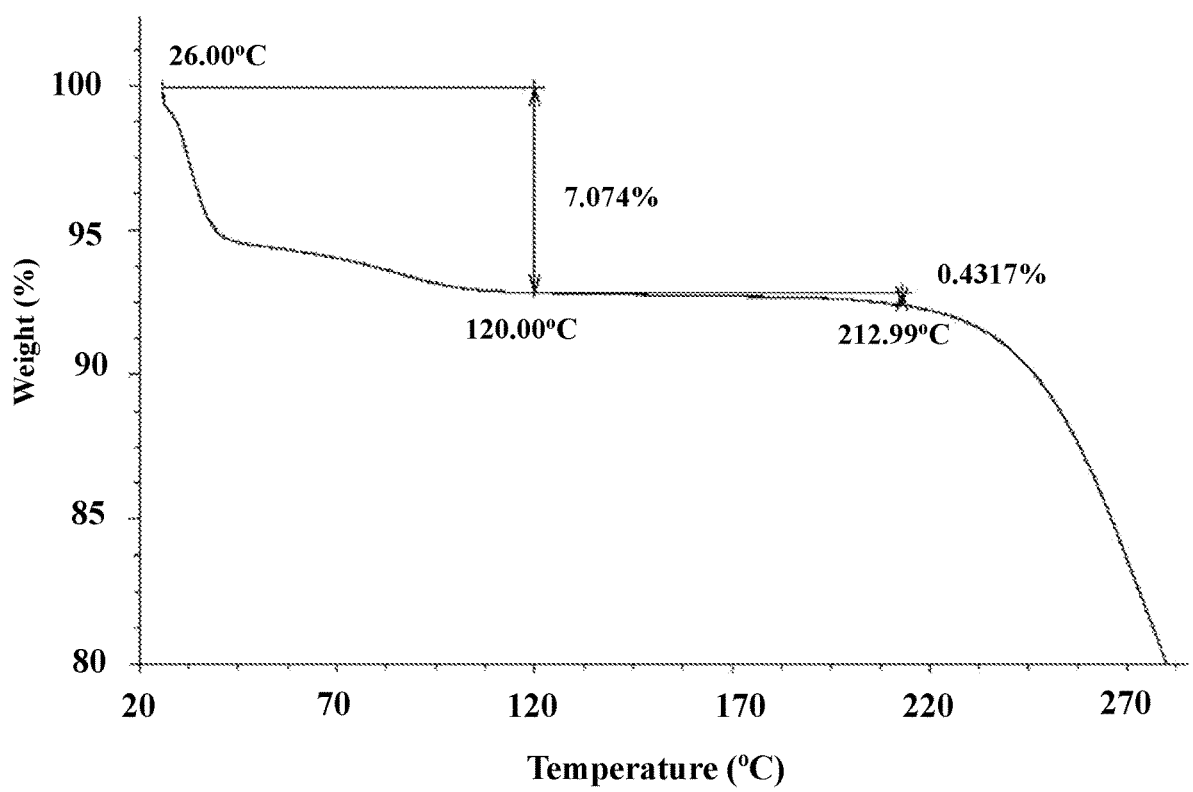
FIG. 3: the TGA pattern of the crystal form A of the compound of formula (I).
Figure 4:
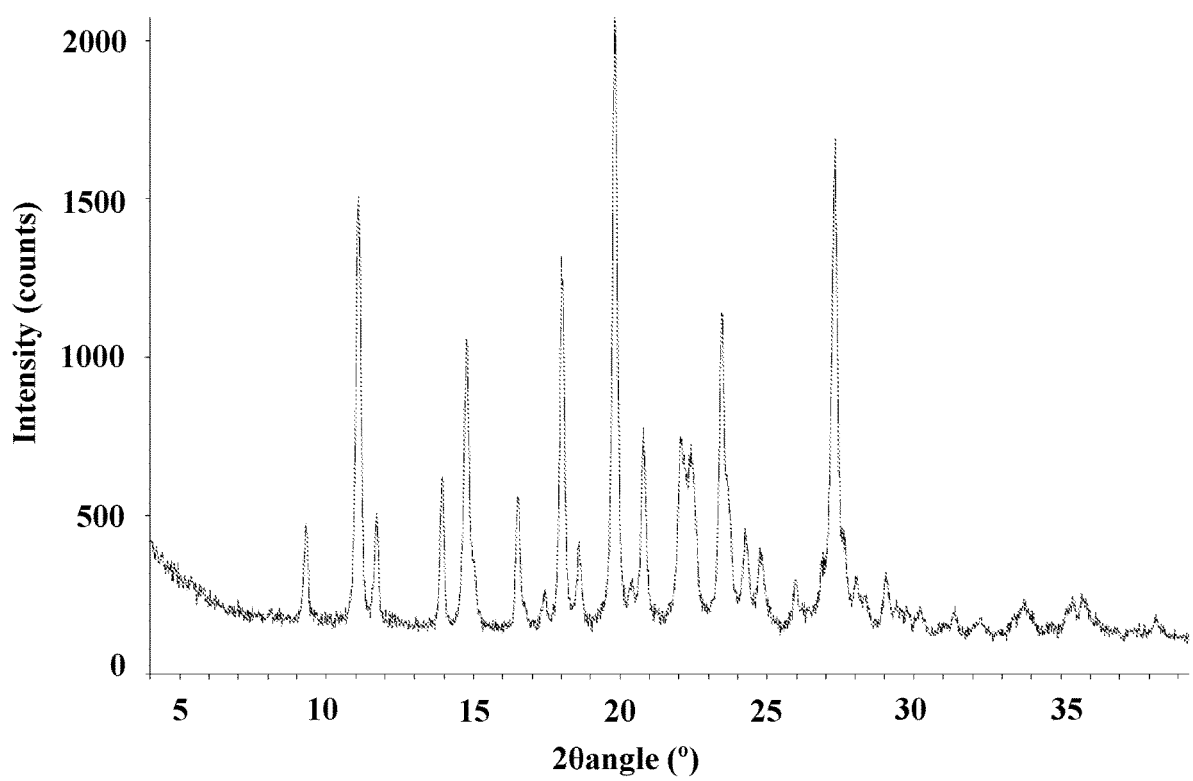
FIG. 4: the XRPD pattern measured by Cu-Kα radiation of the crystal form B of the compound of formula (I).
Figure 5:
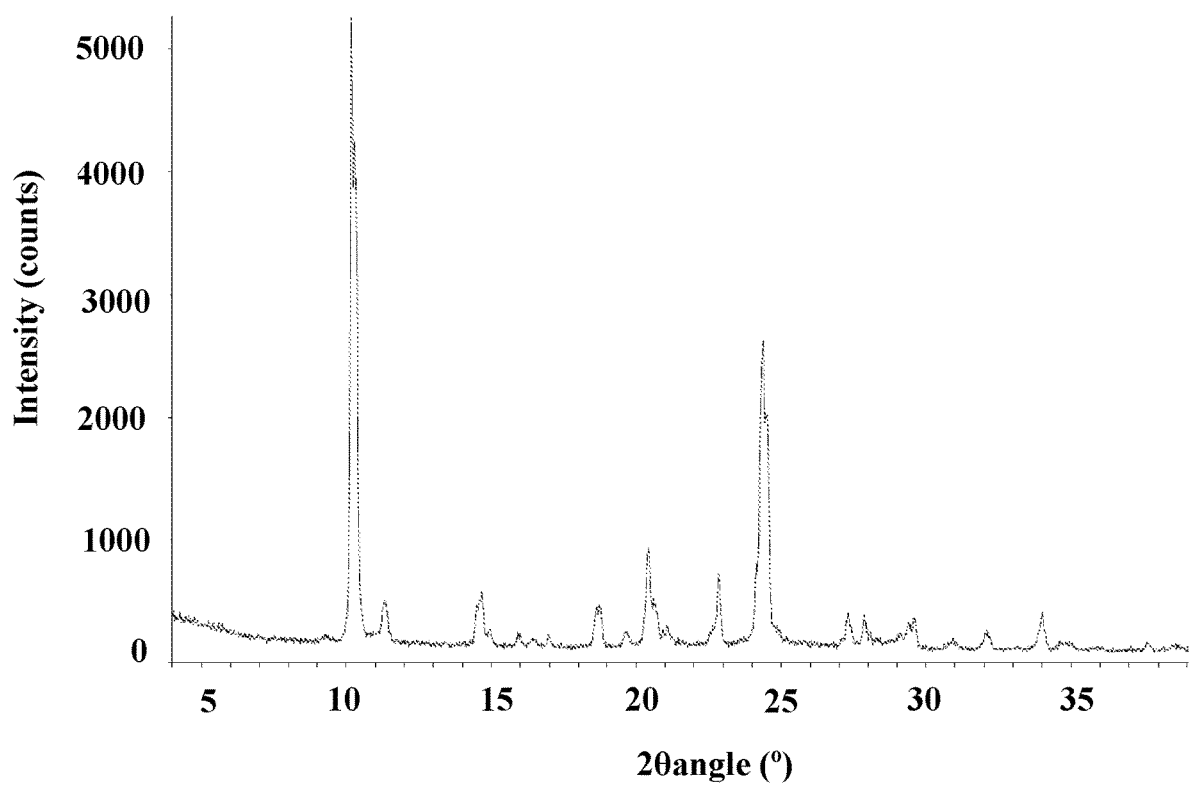
FIG. 5: the XRPD pattern measured by Cu-Kα radiation of the crystal form C of the compound of formula (I).
Figure 6:
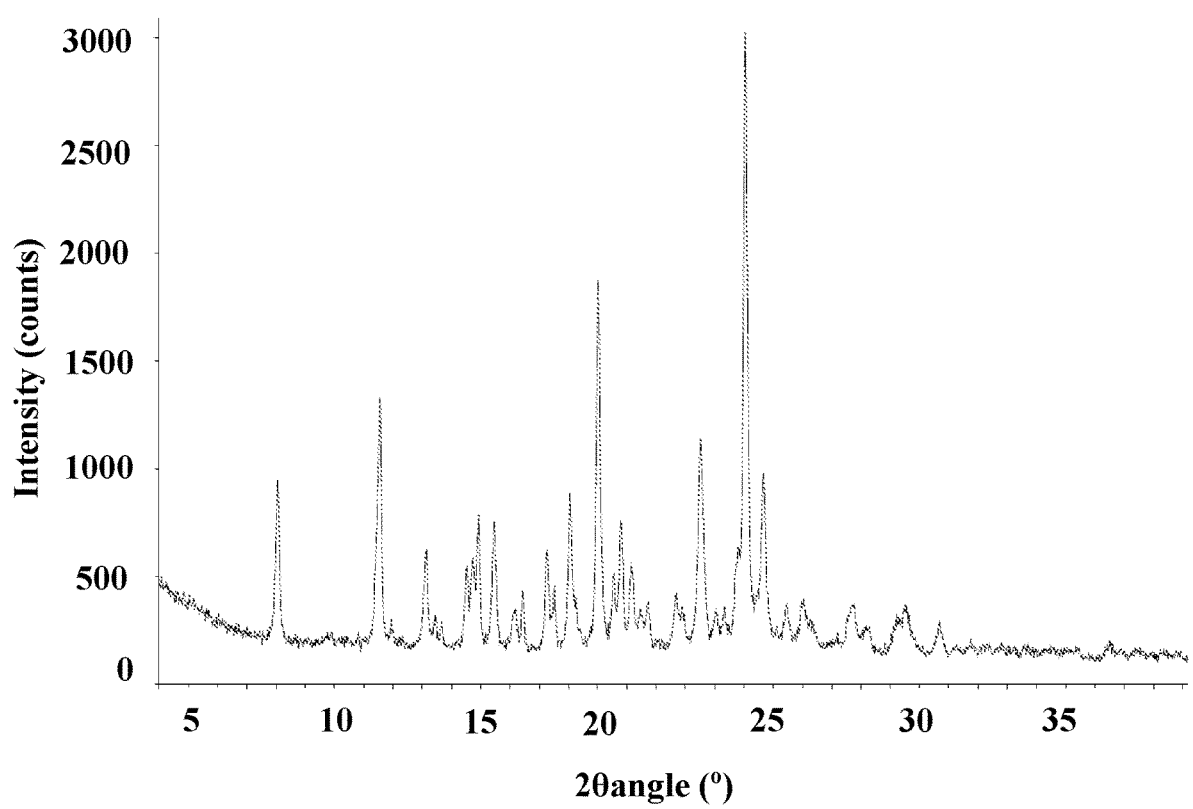
FIG. 6: the XRPD pattern measured by Cu-Kα radiation of the crystal form D of the compound of formula (I).
Figure 7:
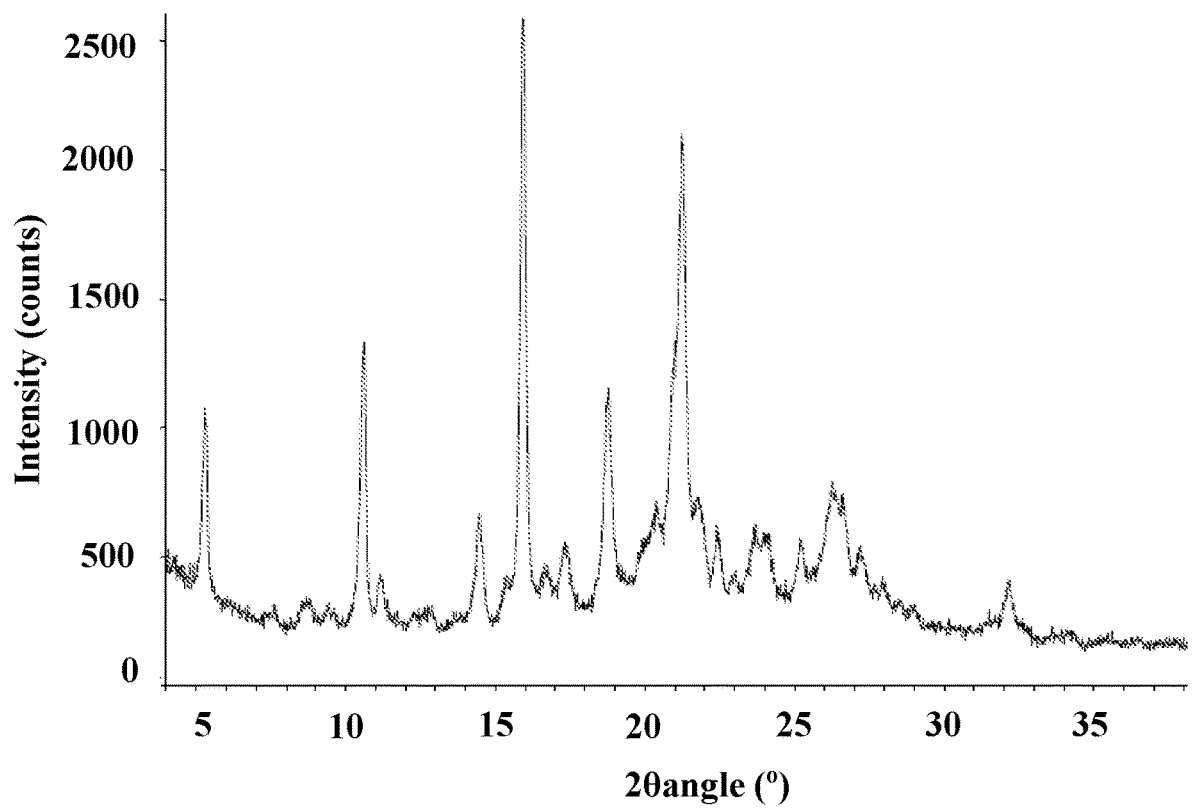
FIG. 7: the XRPD pattern measured by Cu-Kα radiation of the crystal form E of the compound of formula (I).
Figure 8:
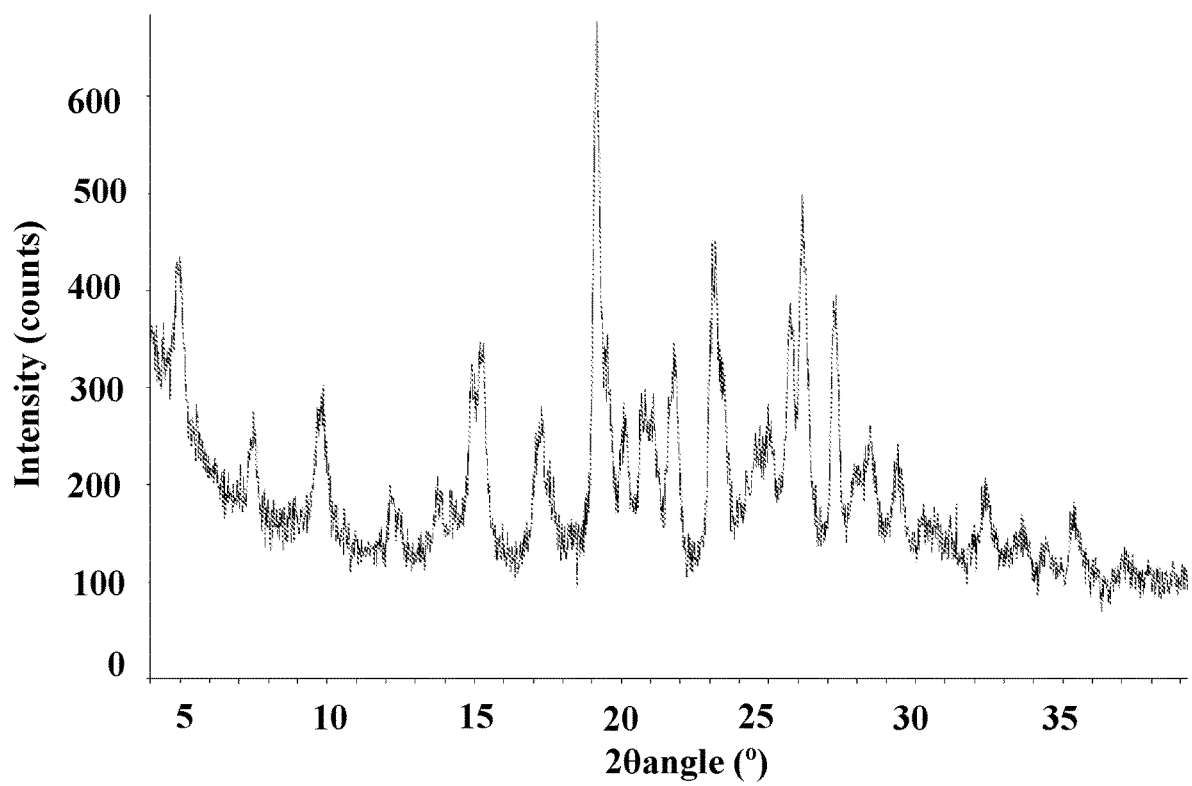
FIG. 8: the XRPD pattern measured by Cu-Kα radiation of the crystal form F of the compound of formula (II).
Figure 9:
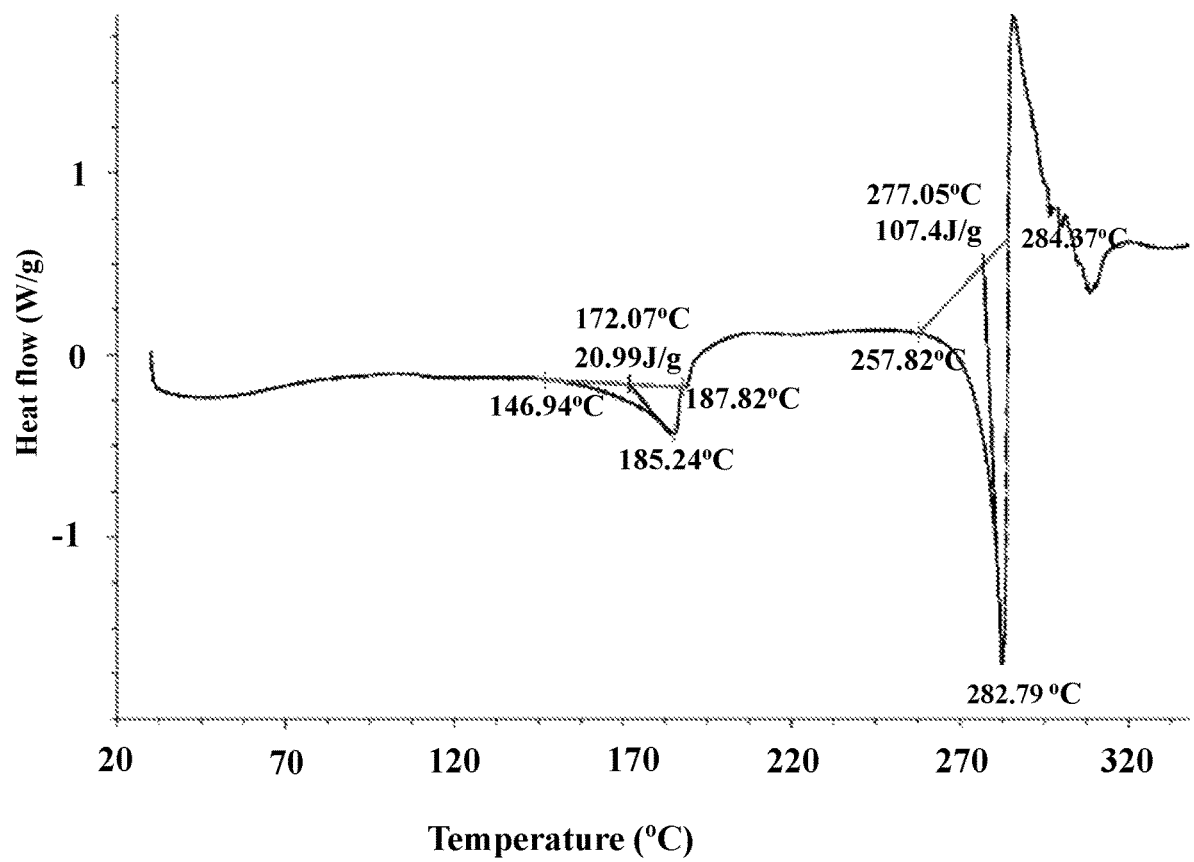
FIG. 9: the DSC pattern of the crystal form F of the compound of formula (II).
Figure 10:
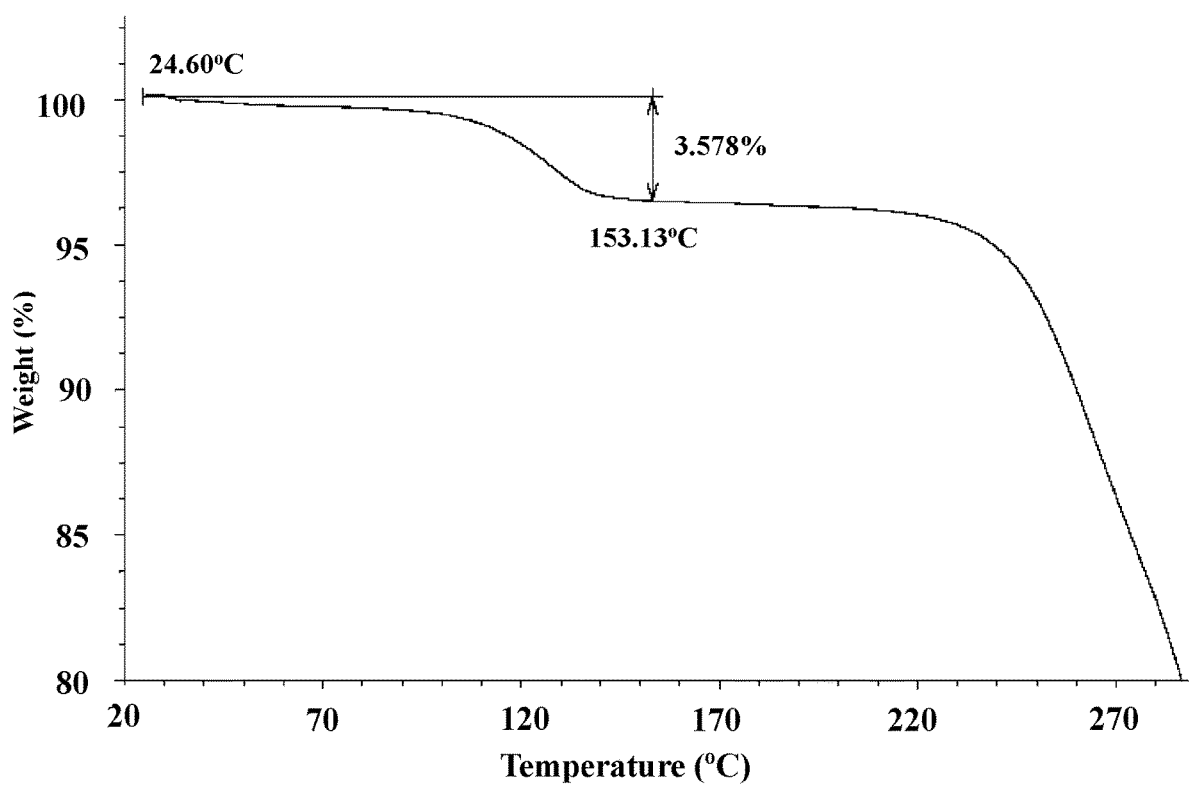
FIG. 10: the TGA pattern of the crystal form F of the compound of formula (II).

In order to better understand the content of the present disclosure, the following embodiments further illustrate the present disclosure, but the present disclosure is not limited thereto.

Synthesis of embodiment 1

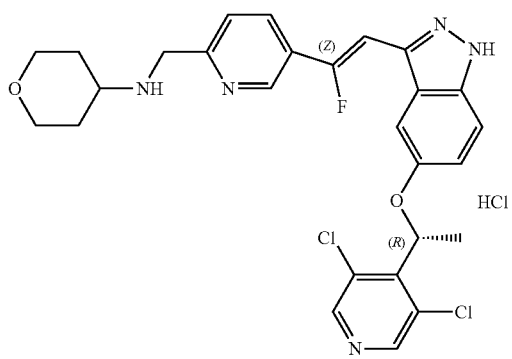

Embodiment 1A

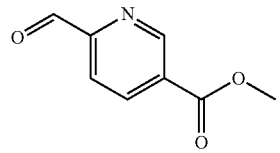

To a solution of methyl 6-carboxylate-1-picoline (20 g, 0.13 mol) in N,N-dimethylsulfoxide (200 mL) were added iodine (33.5 g, 0.13 mmol) and trifluoroacetic acid (35.3 mL, 0.4 mmol) at 0° C. The obtained mixture was stirred for 1 hour and then heated to 140° C. and stirred for 2.5 hours. After being cooled to 0° C., the reaction was terminated with saturated sodium thiosulfate solution (30 mL) and stirred for 30 minutes. The aqueous layer was extracted with ethyl acetate (150 mL×3) and the organic layers were combined and washed with saturated brine (50 mL×2), dried over anhydrous sodium sulfate, filtered, concentrated under reduced pressure and the residue was purified by flash silica gel column chromatography to obtain the embodiment 1A. $^1$H NMR (400 MHz, CHLOROFORM-d) ppm: 10.14 (s, 1H), 9.36 (s, 1H), 8.47 (dd, J=1.3, 8.0 Hz, 1H), 8.03 (d, J=8.0 Hz, 1H), 4.05-3.94 (s,3H).

Embodiment 1B

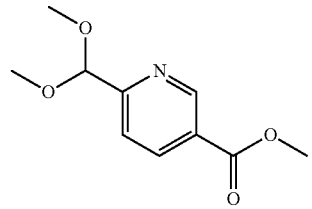

To a solution of the embodiment 1A (20 g, 120 mmol) in trimethyl orthoformate (400 mL) was slowly added formic acid (40 mL) dropwise at 0° C. The obtained mixture were stirred at this temperature for 30 minutes, followed by dropwise addition of concentrated sulfuric acid (1.2 mL). After the addition, the mixture was heated to 50° C. and stirred for 30 minutes, then cooled to 25° C. and stirred for 3 hours, cooled to room temperature, and added to water (100 mL). The aqueous layer was extracted with ethyl acetate (200 mL×3). The organic phases were combined, washed with saturated brine (100 mL×2), dried over anhydrous sodium sulfate, filtered, and concentrated under reduced pressure to obtain the embodiment 1B, which was directly used in the next step.

Embodiment 1C

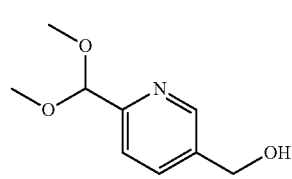

To a solution of the embodiment 1B (8 g, 38 mmol) in tetrahydrofuran (120 mL) was added lithium aluminum hydride (4.4 g, 114 mmol) in portions at 0° C. under the protection of nitrogen. After the addition, the obtained mixture was stirred for 1 hour at this temperature. The reaction was terminated with water (4.4 mL) and 15% sodium hydroxide (4.4 mL) followed by water (13.2 mL), stirred for 30 minutes, filtered and concentrated under reduced pressure to obtain the embodiment 1C, which was directly used in the next step.

Embodiment 1D

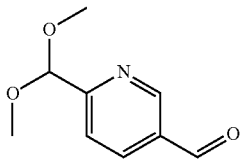

To a solution of the embodiment 1C (5 g, 27 mmol) in dichloromethane (120 mL) was added manganese dioxide (19 g, 216 mmol), and then the obtained mixture was heated to 40° C. and stirred for 16 hours. After being cooled to room temperature, the mixture was filtered and concentrated under reduced pressure. The residue was purified by flash silica gel column chromatography to obtain the embodiment 1D. $^1$H NMR (400 MHz, CHLOROFORM-d) ppm 10.1 (s, 1H), 9.04-9.13 (m, 1H), 8.22 (dd, J=2.01, 8.03 Hz, 1H), 7.75 (d, J=8.03 Hz, 1H), 5.44 (s, 1H), 3.43 (s, 6H).

Embodiment 1E

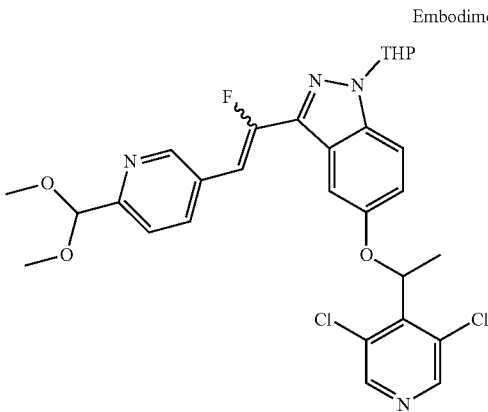

To a solution of the embodiment 1D (2.7 g, 5 mmol) in tetrahydrofuran (80 mL) was added sodium hydride (600 mg, 60%, 14.5 mmol) in portions at 5° C. under nitrogen atmosphere. After the addition, the mixture was stirred for 30 minutes at this temperature, embodiment 1J (2 g, 10.6 mmol) was added thereto, and the mixture was heated to 70° C. and stirred for 16 hours. After being cooled to room temperature, the mixture was poured into ice water (50 mL). The aqueous layer was extracted with ethyl acetate (40 mL×3). The organic phases were combined, washed with saturated brine (20 mL×2), dried over anhydrous sodium sulfate, filtered and concentrated under reduced pressure. The residue was purified by column chromatography to obtain embodiment 1E.

This mixture was resolved by chiral HPLC to obtain cis- and trans-isomers, chiral column: Chiralcel OD-3 150×4.6 mm I.D., 3 μm, mobile phase: ethanol (0.05% DEA)-CO$_2$, from 5% to 40%, Flow rate: 2.5 mL/min, wavelength: 220 nm.

Embodiment 1F

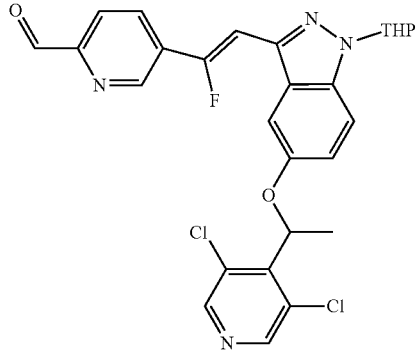

To a mixed solution of embodiment 1E (900 mg, 1.53 mmol) in acetone (4 mL) and water (4 mL) was added p-toluenesulfonic acid monohydrate (291 mg, 1.53 mmol) at room temperature. The reaction solution was heated to 50° C. and stirred for 10 hours. After completion of the reaction, water (4 mL) was added, and dichloromethane (30 mL×3) was added for extraction. The organic phases were combined, washed with saturated brine (20 mL), dried over sodium sulfate, filtered and evaporated to obtain embodiment 1F as yellow solid. LCMS (ESI) m/z: 541 [M+1]$^+$.

Embodiment 1G

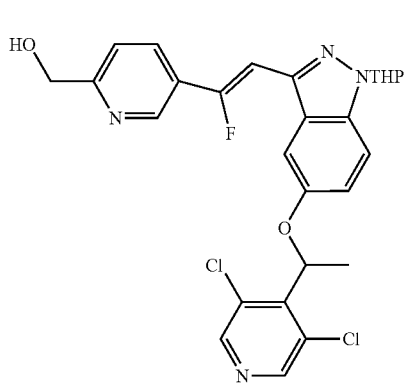

To a solution of embodiment 1F (850 mg, 1.57 mmol) in methanol (8 mL) was added sodium borohydride (119 mg, 3.14 mmol) in portions under nitrogen atmosphere at room temperature. The reaction solution was stirred for 1 hour. Water (30 mL) was added to terminate the reaction and ethyl acetate (40 mL×3) was added for extraction. The organic phases were combined and washed with saturated brine (20 mL), dried over sodium sulfate, filtered and evaporated to obtain embodiment 1G as a yellow liquid. LCMS (ESI) m/z: 543 [M+1]$^+$.

Embodiment 1H

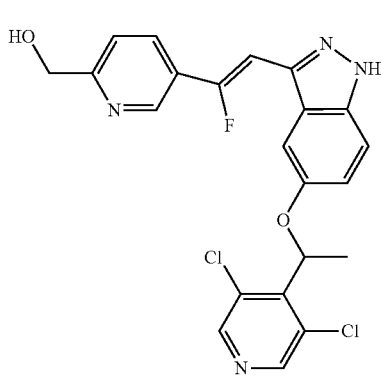

To a solution of embodiment 1G (900 mg, crude product) in methanol (2 mL) was added a freshly prepared solution of acetyl chloride (2 mL) in methanol (6 mL) at room temperature under nitrogen atmosphere. The reaction solution was stirred at 40° C. for 3 hours. The solvent was removed under reduced pressure to obtain the embodiment 1H as a yellow solid. LCMS (ESI) m/z: 459 [M+1]$^+$.

Embodiment 1I

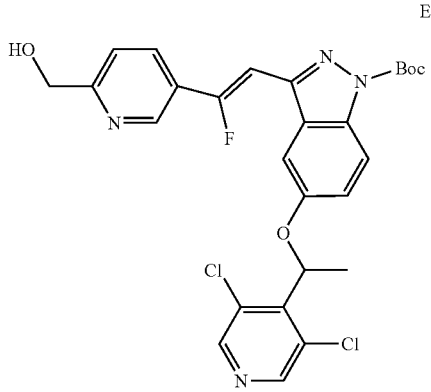

To a solution of the embodiment 1H (748 mg, 1.63 mmol) in dichloromethane (12 mL) were added triethylamine (495 mg, 4.89 mmol), di-tert-butyl dicarbonate (356 mg, 1.63 mmol) and DMAP (20 mg, 0.16 mmol). The obtained reaction solution was stirred at room temperature for 30 minutes. After completion of the reaction, the mixture was adjusted to about pH of 7 with 1M hydrochloric acid, and extracted with dichloromethane (20 mL×3). The organic phases were combined, and washed with saturated brine (20 mL), dried over sodium sulfate, filtered and evaporated, and the residue was purified by flash silica gel column chromatography to obtain embodiment 1I as a yellow solid. LCMS (ESI) m/z: 559 [M+1]$^+$.

Embodiment 1J

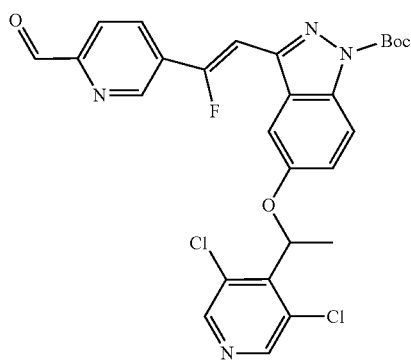

To a solution of the embodiment 1I (280 mg, 0.5 mmol) in dichloromethane (6 mL) was added Dess-Martin reagent (318. mg, 0.75 mmol) in portions at room temperature. The reaction solution was stirred at room temperature for 2 hours. After completion of the reaction, the reaction solution was cooled in an ice-water bath and white solid was precipitated out. The reaction solution was filtered, and the filtrate was evaporated to dryness to obtain embodiment 1J as a yellow solid. LCMS (ESI) m/z: 557 [M+1]$^+$.

Embodiment 1K

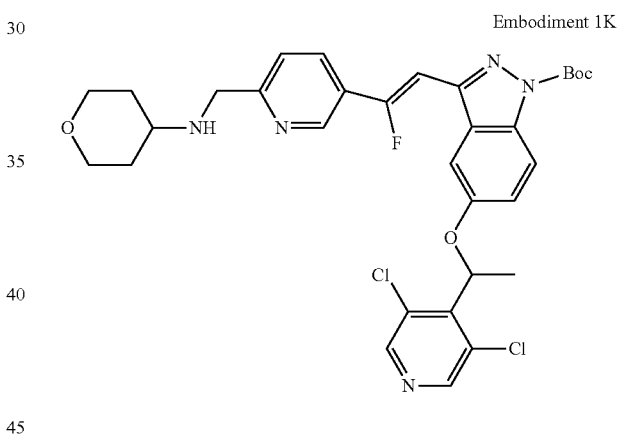

To a solution of embodiment 1J (50 mg, 90 μmol) and tetrahydro-2-hydro-pyran-4-amine (18 mg, 180 μmol) in 1,2-dichloroethane (2.5 mL) was added acetic acid (about 0.1 mL) at room temperature till the pH value of the solution is about 5. The reaction solution was stirred for 2 hours. Sodium cyanoborohydride (12 mg, 180 μmol) was added to the reaction solution at room temperature, and the reaction solution was continued to stir for 1 hour. Water (5 mL) was added to a reaction solution, followed by addition of dichloromethane (20 mL×3) for extraction. The organic phases were combined, washed with saturated brine (20 mL), dried over sodium sulfate, filtered and evaporated, and the residue was purified by flash silica gel column chromatography to obtain embodiment 1K. The solid sample was subjected to chiral column resolution to obtain embodiment 1K-R configuration (8 mg) and embodiment 1K-S configuration (8 mg).

LCMS (ESI) m/z: 642 [M+1]$^+$.

Chiral column method: Chiral column, Chiralcel OJ-H 250×4.6 mm I.D., 5 μm; mobile phase, methanol (0.05% DEA (diethylamine))-CO$_2$ from 5% to 40%; flow rate, 2.35 mL/min; wavelength, 280 nm.

Embodiment 1L

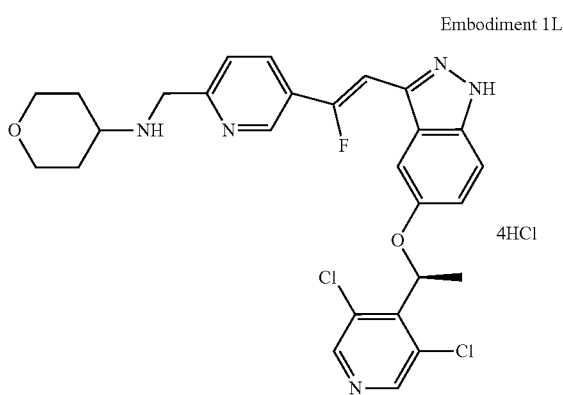 [SMILES: C[C@H](Oc1ccc2[nH]nc(/C=C(\F)c3ccc(CNC4CCOCC4)nc3)c2c1)c1c(Cl)cncc1Cl]

To a solution of embodiment 1K-S configuration (15 mg, 23 μmol) (15 mg product of 1K-S configuration was obtained by an amplified reaction of 200 mg scale according to the preparation method of embodiment 1K) in methanol (1 mL) was added a freshly prepared solution of acetyl chloride (1 mL) in methanol (3 mL) under nitrogen atmosphere at room temperature. The reaction solution was stirred at 40° C. for 3 hours. The solution was removed under vacuum to obtain the embodiment 1L. LCMS (ESI) m/z: 542 [M+1]$^+$. $^1$H NMR (400 MHz, METHANOL-$d_4$) ppm 9.04 (s, 1H), 8.50 (br. s., 2H), 8.23 (d, J=7.03 Hz, 1H), 7.64 (d, J=8.03 Hz, 1H), 7.49 (d, J=8.53 Hz, 1H), 7.18-7.26 (m, 2H), 7.04 (s, 2H), 6.12 (q, J=6.53 Hz, 1H), 4.53 (s, 2H), 4.08 (dd, J=4.02, 11.54 Hz, 2H), 3.56-3.66 (m, 7H), 2.15 (d, J=11.04 Hz, 2H), 1.83 (d, J=6.53 Hz, 4H), 1.18 (t, J=7.03 Hz, 9H).

Embodiment 1

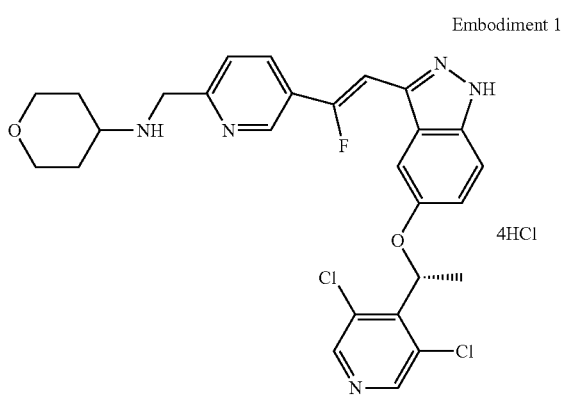 [SMILES: C[C@@H](Oc1ccc2[nH]nc(/C=C(\F)c3ccc(CNC4CCOCC4)nc3)c2c1)c1c(Cl)cncc1Cl]

As the method described in the embodiment 1L, a freshly prepared solution of acetyl chloride (1 mL) in methanol (3 mL) was added to a solution of the embodiment 1K-R configuration (15 mg, 23 μmol) (15 mg product of 1K-R configuration was obtained by an amplified reaction of 200 mg scale) in methanol (1 mL) under nitrogen atmosphere at room temperature. The reaction solution was stirred at 40° C. for 3 hours. The solution was removed under vacuum to obtain embodiment 1. LCMS (ESI) m/z: 542[M+1]$^1$. $^1$H NMR (400 MHz, METHANOL-$d_4$) ppm 8.95-9.12 (m, 1H), 8.44-8.59 (m, 1H), 8.25 (br. s., 1H), 7.68 (br. s., 1H), 7.51 (d, J=8.78 Hz, 1H), 7.25 (d, J=15.06 Hz, 2H), 6.91-7.10 (m, 1H), 6.13 (d, J=5.77 Hz, 1H), 4.54 (br. s., 2H), 4.07 (d, J=10.54 Hz, 2H), 3.42-3.57 (m, 3H), 2.15 (d, J=10.79 Hz, 2H), 1.83 (m, 5H).

The embodiment 1 was dissolved in methanol, dissociated with a saturated aqueous solution of sodium bicarbonate, and extracted with dichloromethane. The organic phase was subjected to rotary evaporation to dryness to obtain a compound of formula (I).

Embodiment 2: Preparation of Crystal Form A of the Compound of Formula (I)

The embodiment 1 was dissolved in methanol, dissociated with a saturated aqueous solution of sodium bicarbonate, and extracted with dichloromethane. The organic phase was subjected to rotary evaporation to dryness, followed by slurrying with a small amount of methanol for purification, and was filtered to obtain a solid. XRPD was used to detect the state of the crystal form, and the crystal form A of the compound of formula (I) was obtained.

Embodiment 3: Preparation of Crystal Form B of the Compound of Formula (I)

30 mg of the compound of formula (I) was weighed and added into a glass bottle, followed by addition of 400 μL of methanol to obtain a suspension. The suspension sample was placed on a magnetic stirrer (40° C.) and subjected to a stirring test under darkness. The suspension sample was stirred at 40° C. for 2 days and then centrifuged, and then the residual sample was placed in a vacuum oven (40° C.) and dried overnight. XRPD was used to detect the state of the crystal form, and the crystal form B of the compound of formula (I) was obtained.

Embodiment 4: Preparation of Crystal Form C of the Compound of Formula (I)

30 mg of the compound of formula (I) was weighed and added into a glass bottle, followed by addition of 400 μL of ethyl acetate-ethanol (3:2) to obtain a suspension. The suspension sample was placed on a magnetic stirrer (40° C.) and subjected to a stirring test under darkness. The suspension sample was stirred at 40° C. for 2 days and then centrifuged, and then the residual sample was placed in a vacuum oven (40° C.) and dried overnight. XRPD was used to detect the state of the crystal form, and the crystal form C of the compound of formula (I) was obtained.

Embodiment 5: Preparation of Crystal Form D of the Compound of Formula (I)

30 mg of the compound of formula (I) was weighed and added into a glass bottle, followed by addition of 400 μL of acetone to obtain a suspension. The suspension sample was placed on a magnetic stirrer (40° C.) and subjected to a stirring test under darkness. The suspension sample was stirred at 40° C. for 2 days and then centrifuged, and then the residual sample was placed in a vacuum oven (40° C.) and dried overnight. XRPD was used to detect the state of the crystal form, and the crystal form D of the compound of formula (I) was obtained.

Embodiment 6: Preparation of Crystal Form E of the Compound of Formula (I)

30 mg of the compound of formula (I) was weighed and added into a glass bottle, followed by addition of 400 μL of isopropanol to obtain a suspension. The suspension sample was placed on a magnetic stirrer (40° C.) and subjected to a stirring test under darkness. The suspension sample was stirred at 40° C. for 2 days and then centrifuged, and then the residual sample was placed in a vacuum oven (40° C.) and dried overnight. XRPD was used to detect the state of the crystal form, and the crystal form E of the compound of formula (I) was obtained.

Embodiment 7: Preparation of Crystal Form F of the Compound of Formula (II)

60 mg of the compound of formula (I) was weighed and added into a glass bottle with a magnetic stir bar The glass bottle was placed on a magnetic stirrer. 1.8 mL of ethyl acetate was added and the obtained mixture was heated to 50° C. to obtain a clear solution. An appropriate amount of a solution of hydrochloric acid in ethanol (1.2 mL) was slowly added (with the molar ratio of the compound of formula (I) to acid of 1:2), and observed. After the addition of hydrochloric acid, the solution was stirred at 50° C. for 2 hours, and stirred at room temperature overnight. Precipitation was formed, and the solution was centrifuged. Then, the residual sample was placed in a vacuum oven (40° C.) and dried. XRPD was used to detect the state of the crystal form, and the crystal form F of the compound of formula (II) was obtained.

Embodiment 8: Preparation of Crystal Form G of the Compound of Formula (II)

30 mg of hydrochloride of the compound of formula (I) (embodiment 1) was weighed and placed in a glass bottle, and 400 μL of methanol was added. The dissolved sample was quickly centrifuged. The supernatant was placed in a centrifuge tube, and the centrifuge tube was sealed with an aluminum foil poked with pinholes. The centrifuge tube was placed in a fume hood for volatilization. The suspension sample was placed on a magnetic stirrer, stirred (40° C.) (in dark), and quickly centrifuged after 2 days. The supernatant was placed in a fume hood to volatilize to dryness. The residual sample obtained by centrifugation and the solid obtained by volatilization were collected and dried in a vacuum oven at 30° C. overnight. XRPD was used to detect the state of the crystal form, and the crystal form G of the compound of formula (II) was obtained.

Embodiment 9: Preparation of Crystal Form G of the Compound of Formula (II)

Ethanol (1.25 L) was added to the three-necked flask (3 L) containing the compound of formula (I) (41.7 g); the reaction solution was heated to 90° C., and hydrochloric acid/ethyl acetate (38.4 mL) was added dropwise to the flask. After stirring at 90° C. for 2 hours, the reaction solution was cooled to room temperature and stirred for 20 hours; the reaction solution was filtered, and the obtained solid was washed with 0.1 L of ethanol; the finally obtained solid was treated by a rotary evaporator (50° C., 6 hours) to remove a small amount of ethanol contained therein to obtain the crystal form G of the compound of formula (II).

Embodiment 10: Preparation of Crystal Form H of the Compound of Formula (II)

30 mg of the hydrochloride of the compound of formula (I) (embodiment 1) was weighed and placed in a glass bottle, and 400 μL of ethanol was added. The dissolved sample was quickly centrifuged, and the supernatant was placed in a centrifuge tube. The centrifuge tube was sealed with an aluminum foil poked with pinholes. The centrifuge tube was placed in a fume hood for volatilization. The suspension sample was placed on a magnetic stirrer, stirred (40° C.) (in dark), and quickly centrifuged after 2 days. The supernatant was placed in a fume hood to volatilize to dryness. The residual sample obtained by centrifugation and the solid obtained by volatilization were collected and dried in a vacuum oven at 30° C. overnight. XRPD was used to detect the state of the crystal form, and the crystal form H of the compound of formula (II) was obtained.

Embodiment 11: Preparation of Crystal Form I of the Compound of Formula (III)

60 mg of the compound of formula (I) was weighed and added into a glass bottle with a magnetic stir bar. The glass bottle was placed on a magnetic stirrer. 1.8 mL of ethyl acetate was added and the obtained mixture was heated to 50° C. to obtain a clear solution. An appropriate amount of a solution of citric acid in ethanol (1.2 mL) was slowly added (with the molar ratio of the compound of formula (I) to acid of 1:2), and observed. After the addition of hydrochloric acid, the solution was stirred at 50° C. for 2 hours, and stirred at room temperature overnight. Precipitation was formed, and the solution was centrifuged. Then, the residual sample was placed in a vacuum oven (40° C.) and dried. XRPD was used to detect the state of the crystal form, and the crystal form I of the compound of formula (III) was obtained.

Embodiment 12: Preparation of Crystal Form J of the Compound of Formula (IV)

60 mg of the compound of formula (I) was weighed and added into a glass bottle with a magnetic stir bar. The glass bottle was placed on a magnetic stirrer. 1.8 mL of ethyl acetate was added and the obtained mixture was heated to 50° C. to obtain a clear solution. An appropriate amount of a solution of L-malic acid in ethanol (1.2 mL) was slowly added (with the molar ratio of the compound of formula (I)

to acid of 1:2), and observed. After the addition of hydrochloric acid, the solution was stirred at 50° C. for 2 hours, and stirred at room temperature overnight. Precipitation was formed, and the solution was centrifuged. Then, the residual sample was placed in a vacuum oven (40° C.) and dried. XRPD was used to detect the state of the crystal form, and the crystal form J of the compound of formula (IV) was obtained.

TEST EXAMPLE 1: SOLUBILITY TEST OF COMPOUNDS OF FORMULA (I), (II), (III) OR (IV)

Preparation of Control Sample Solution (Using Compound of Formula (I) as Control Sample)

About 5 mg of the compound of formula (I) was weighed accurately, and placed in a sample bottle. 10 mL of acetonitrile was added. The mixture was sonicated for 5 minutes, cooled to room temperature, and well mixed. Two control sample solutions were prepared in parallel, and labeled as STD-1 and STD-2, respectively.

Preparation of Linear Solution

The control sample solution STD-1 was serially diluted 1, 5, 10, 100 and 1000 times and labeled as linear solutions L1, L2, L3, L4 and L5.

Solubility Test of Compound (I) and Its Salt

The solubility of the compound of formula (I) and its salt in 4 vehicles with different pH were tested. About 10 mg of the compounds of formula (I)-(IV) were weighed respectively, then 5.0 mL of different vehicles (water, SGF, FaSSIF, FeSSIF) were added thereto, respectively, and well mixed to obtain suspensions. Magnetic stir bars were added into the suspensions, and the suspensions were placed on a magnetic stirrer for stirring. After stirring for 2 hours, 4 hours, and 24 hours, the samples were collected and centrifuged. The residual solid samples in the lower layer were detected by XRPD. The concentrations of the samples in the upper layer were determined by HPLC, and the pH value of the samples were also detected. The results of the solubility test are as shown in Table 12 and Table 13.

FaSSIF: (1) 0.042 g of sodium hydroxide, 0.3438 g of sodium dihydrogen phosphate and 0.6186 g of sodium chloride were weighed, and 90 mL of purified water was added and well mixed. The pH value of the obtained solution were adjusted to 6.5 with 1 N hydrochloric acid or 1 N sodium hydroxide, and the solution were diluted with purified water to a final volume of 100 mL. (2) 50 mL of the above buffer solution was taken, followed by addition of 0.224 g of commercially available FaSSIF/FeSSIF/FaSSGF powder (Biorelevant.com). The buffer solution was stirred until dissolved, and diluted with purified water to a final volume of 100 mL. The buffer solution was placed at room temperature. After standing for two hours, the buffer solution was observed to be slightly milky white and was ready for use.

FeSSIF: (1) 0.404 g of sodium hydroxide, 0.865 g of glacial acetic acid, 1.1874 g of sodium chloride were weighed, and 90 mL of purified water was added and well mixed. The pH value of the obtained solution were adjusted to 5.0 with 1 N hydrochloric acid or 1 N sodium hydroxide, and the solution were diluted with purified water to a final volume of 100 mL. (2) 50 mL of the above buffer solution was taken, followed by addition of 1.12 g of commercially available FaSSIF/FeSSIF/FaSSGF powder (Biorelevant.com). The buffer solution was stirred until dissolved, and diluted with purified water to a final volume of 100 mL. The buffer solution was placed at room temperature. After standing for two hours, the buffer solution was observed to be a transparent liquid, and was ready for use.

FaSSGF (SGF): (1) 0.2 g of sodium chloride was added to 90 mL of purified water and mixed well. The pH value thereof was adjusted to 1.8 with 1 N hydrochloric acid and the solution diluted with purified water to a final volume of 100 mL. The obtained solution was allowed to stand at room temperature.

TABLE 12

Solubility test result of the compounds of formula (I) and (II) in 4 vehicles

| | The compound of formula (I) | | | | The compound of formula (II) | | | |
|---|---|---|---|---|---|---|---|---|
| Vehicle | $H_2O$ | SGF | FaSSIF | FeSSIF | $H_2O$ | SGF | FaSSIF | FeSSIF |
| pH(vehicle) | 8.23 | 1.57 | 6.62 | 4.59 | 8.23 | 1.57 | 6.62 | 4.59 |
| pH (4 hours) | 8.33 | 2.10 | 6.58 | 5.01 | 2.68 | 1.86 | 6.25 | 4.90 |
| pH (24 hours) | 7.97 | 2.06 | 6.57 | 5.01 | 2.68 | 1.86 | 6.22 | 4.91 |
| Solubility (µg/mL)_4 hours | 5.8 | 1971.3 | 781.0 | 1948.4 | 1576.9 | 106.3 | 949.7 | 2010.0 |
| Solubility (µg/mL)_24 hours | <LOQ | 1825.6 | 611.3 | 1726.2 | 1540.9 | 45.4 | 281.6 | 1831.5 |

Note:
<LOQ means below detection limit

TABLE 13

Solubility test results of compounds of formula (III) and (IV) in 4 vehicles

| | The compound of formula (III) | | | | The compound of formula (IV) | | | |
|---|---|---|---|---|---|---|---|---|
| Vehicle | H$_2$O | SGF | FaSSIF | FeSSIF | H$_2$O | SGF | FaSSIF | FeSSIF |
| pH(Vehicle) | 8.23 | 1.57 | 6.62 | 4.59 | 8.23 | 1.57 | 6.62 | 4.59 |
| pH(4 hours) | 5.60 | 2.09 | 6.43 | 4.96 | 6.93 | 2.09 | 6.26 | 4.95 |
| pH(24 hours) | 5.47 | 2.08 | 6.33 | 4.97 | 6.46 | 2.09 | 6.27 | 4.95 |
| Solubility (μg/mL)_4 hours | 99.5 | 2422.6 | 910.0 | 2373.7 | 7.4 | 2470.7 | 1127.3 | 2410.4 |
| Solubility (μg/mL)_24 hours | 183.9 | 16.8 | 941.5 | 2229.7 | 19.3 | 43.3 | 823.6 | 2281.9 |

Conclusion: the solubility data of the salts in biological vehicle show that the hydrochloride has the highest solubility in the aqueous phase, and the three salts have similar solubility in simulated intestinal fluid and simulated gastric fluid; and the free base has good solubility in the three biological vehicle, but is extremely difficult to dissolve in water.

TEST EXAMPLE 2: SOLID STABILITY TEST OF CRYSTAL FORM G, CRYSTAL FORM I AND CRYSTAL FORM J

About 10 mg of crystal form G, crystal form I, or crystal form J were weighed accurately, and placed on the bottom of a 40 mL glass sample bottle and spread into a thin layer. For an open sample, the bottle mouth thereof was sealed with aluminum foil poked with pinholes to ensure that the sample can fully contact with the ambient air. For a sealed sample, the bottle mouth thereof was sealed with a bottle cap, and wrapped with a sealing film. Two duplicate samples were weighed at each time point of each condition in parallel, and an appropriate amount of sample (not weighed) was taken additionally for XRPD detection. The prepared samples were placed under each condition and were sampled and analyzed when the time point was arrived. On 0$^{th}$ day, 5 control samples were weighed in parallel and stored in a refrigerator at −20° C. until analysis. The samples subjected to light irradiation were prepared by the same method, and placed on the bottom of a 40 mL glass sample bottle. The glass bottle was left open and placed in the upright position in a light irradiation box. In addition, two samples in an appropriate amount were taken as samples in dark, and the glass bottles containing the same were left open, put in the upright position, and wrapped with tin foil, and irradiated with a total luminance of 1.2×10$^6$Lux.hr and a near ultraviolet power of 200 w.hr/m$^2$. After irradiation, the samples was stored in the refrigerator at −20° C. for analysis.

The compounds were placed under the following conditions and sampled at different time points to detect the physical properties, and the content and total impurities were analyzed by HPLC. The research conditions and testing items are shown in Table 14 to Table 16.

TABLE 14

Solid stability test of crystal form G of the compound of formula (II)

| Test condition | Time point | Appearance | Crystal form (XRPD) | Content (%) | Total impurities (%) |
|---|---|---|---|---|---|
| — | 0$^{th}$ day | Earth yellow powder | Crystal form G | 100 | 0.11 |
| High temperature (60° C., open) | 5$^{th}$ day | Earth yellow powder | Crystal form G | 102.02 | 0.16 |
| | 10$^{th}$ day | Earth yellow powder | Crystal form G | 100.14 | 0.16 |
| High humidity (Room temperature/ relative humidity 92.5%, open) | 5$^{th}$ day | Earth yellow powder | Crystal form G | 100.82 | 0.11 |
| | 10$^{th}$ day | Earth yellow powder | Crystal form G | 98.79 | 0.11 |
| Light irradiation (total illuminance: 1.2 × 10$^6$ Lux · hr: near ultraviolet: 200 w · hr/m$^2$, open) | Light irradiation | Earth yellow powder | Crystal form G | 102.93 | 0.37 |
| | Dark | Earth yellow powder | Crystal form G | 101.69 | 0.11 |
| Accelerated test (40 C./relative humidity 75%, open) | 10$^{th}$ day | Earth yellow powder | Crystal form G | 99.97 | 0.11 |
| | 1$^{st}$ month | Earth yellow powder | Crystal form G | 102.45 | 0.16 |
| | 2$^{nd}$ month | Earth yellow powder | Crystal form G | 101.07 | 0.17 |
| | 3$^{rd}$ month | Earth yellow powder | Crystal form G | 98.81 | 0.18 |
| Accelerated test (60° C./relative humidity 75%, open) | 10$^{th}$ day | Earth yellow powder | Crystal form G | 98.38 | 0.15 |
| | 1$^{st}$ month | Earth yellow powder | Crystal form G | 101.51 | 0.17 |

TABLE 14-continued

Solid stability test of crystal form G of the compound of formula (II)

| Test condition | Time point | Appearance | Crystal form (XRPD) | Content (%) | Total impurities (%) |
|---|---|---|---|---|---|
| | $2^{nd}$ month | Earth yellow powder | Crystal form G | 99.86 | 0.18 |
| | $3^{rd}$ month | Earth yellow powder | Crystal form G | 100.21 | 0.19 |

TABLE 15

Solid stability test of crystal form I of the compound of formula (III)

| Test condition | Time point | Appearance | Crystal form (XRPD) | Content (%) | Total impurities (%) |
|---|---|---|---|---|---|
| — | $0^{th}$ day | Earth yellow powder | Crystal form I | 100.00 | 1.91 |
| High temperature (60° C., open) | $5^{th}$ day | Earth yellow powder | Crystal form I | 100.40 | 1.93 |
| | $10^{th}$ day | Earth yellow powder | Crystal form I | 100.26 | 1.83 |
| High humidity (Room temperature/ relative humidity 92.5%, open) | $5^{th}$ day | Earth yellow powder | Crystal form I | 99.10 | 1.88 |
| | $10^{th}$ day | Earth yellow powder | Crystal form I | 99.92 | 1.73 |
| Light irradiation (total illuminance: 1.2 × 10$^6$ Lux · hr/ near ultraviolet: 200 w · hr/m$^2$, open) | Light irradiation | Earth yellow powder | Crystal form I | 97.37 | 2.35 |
| | Dark | Earth yellow powder | Crystal form I | 99.42 | 1.85 |
| Accelerated test (40° C./relative humidity 75%, open) | $10^{th}$ day | Earth yellow powder | Crystal form I | 99.93 | 1.85 |
| | $1^{st}$ month | Earth yellow powder | Crystal form I | 99.83 | 1.88 |
| | $2^{nd}$ month | Earth yellow powder | Crystal form I | 100.06 | 1.82 |
| | $3^{rd}$ month | Earth yellow powder | Crystal form I | 99.32 | 1.86 |
| Accelerated test (60° C./relative humidity 75%, open) | $10^{th}$ day | Earth yellow powder | Crystal form I | 100.19 | 1.85 |
| | $1^{st}$ month | Earth yellow powder | Crystal form I | 99.95 | 1.74 |
| | $2^{nd}$ month | Earth yellow powder | Crystal form I | 98.46 | 1.79 |
| | $3^{rd}$ month | Earth yellow powder | Crystal form I | 97.31 | 1.83 |

TABLE 16

Solid stability test of crystal form J of the compound of formula (IV)

| Test condition | Time point | Appearance | Crystal form (XRPD) | Content (%) | Total impurities (%) |
|---|---|---|---|---|---|
| — | $0^{th}$ day | Earth yellow powder | Crystal form J | 100.00 | 1.42 |
| High temperature (60° C., open) | $5^{th}$ day | Earth yellow powder | Crystal form J | 98.83 | 1.39 |
| | $10^{th}$ day | Earth yellow powder | Crystal form J | 99.11 | 1.46 |
| High humidity (Room temperature/ relative humidity 92.5%, open) | $5^{th}$ day | Earth yellow powder | Crystal form J | 99.06 | 1.31 |
| | $10^{th}$ day | Earth yellow powder | Crystal form J | 100.58 | 1.32 |
| Light irradiation (total illuminance: | Light irradiation | Earth yellow powder | Crystal form J | 96.41 | 1.90 |

TABLE 16-continued

Solid stability test of crystal form J of the compound of formula (IV)

| Test condition | Time point | Appearance | Crystal form (XRPD) | Content (%) | Total impurities (%) |
|---|---|---|---|---|---|
| $1.2 \times 10^6$ Lux · hr/ near ultraviolet: 200 w · hr/m², open) | Dark | Earth yellow powder | Crystal form J | 98.04 | 1.30 |
| Accelerated test (40 C./relative humidity 75%, open) | $10^{th}$ day | Earth yellow powder | Crystal form J | 99.44 | 1.33 |
| | $1^{st}$ month | Earth yellow powder | Crystal form J | 99.31 | 1.36 |
| | $2^{nd}$ month | Earth yellow powder | Crystal form J | 99.40 | 1.20 |
| | $3^{rd}$ month | Earth yellow powder | Crystal form J | 98.62 | 1.20 |
| Accelerated test (60 C./relative humidity 75%, open) | $10^{th}$ day | Earth yellow powder | Crystal form J | 99.05 | 1.36 |
| | $1^{st}$ month | Earth yellow powder | Crystal form J | 97.07 | 1.43 |
| | $2^{nd}$ month | Earth yellow powder | Crystal form J | 97.22 | 1.48 |
| | $3^{rd}$ month | Earth yellow powder | Crystal form J | 97.18 | 1.53 |

Conclusion: both the influencing factors and accelerated tests show that the crystal form G, I and J have excellent thermal stability and stability under accelerated conditions, generate slight impurities under light irradiation conditions, and exhibit good stability under dark conditions.

TEST EXAMPLE 3: HYGROSCOPICITY TEST OF THE CRYSTAL FORM I OF THE COMPOUND OF FORMULA (III)

Experimental Materials

SMS DVS Advantage dynamic vapor sorption analyzer

Experimental Method 10 to 15 mg of the crystal form I of the compound of formula (III) was taken and placed in a DVS sample tray for testing.

Experimental Results

Figure 20:
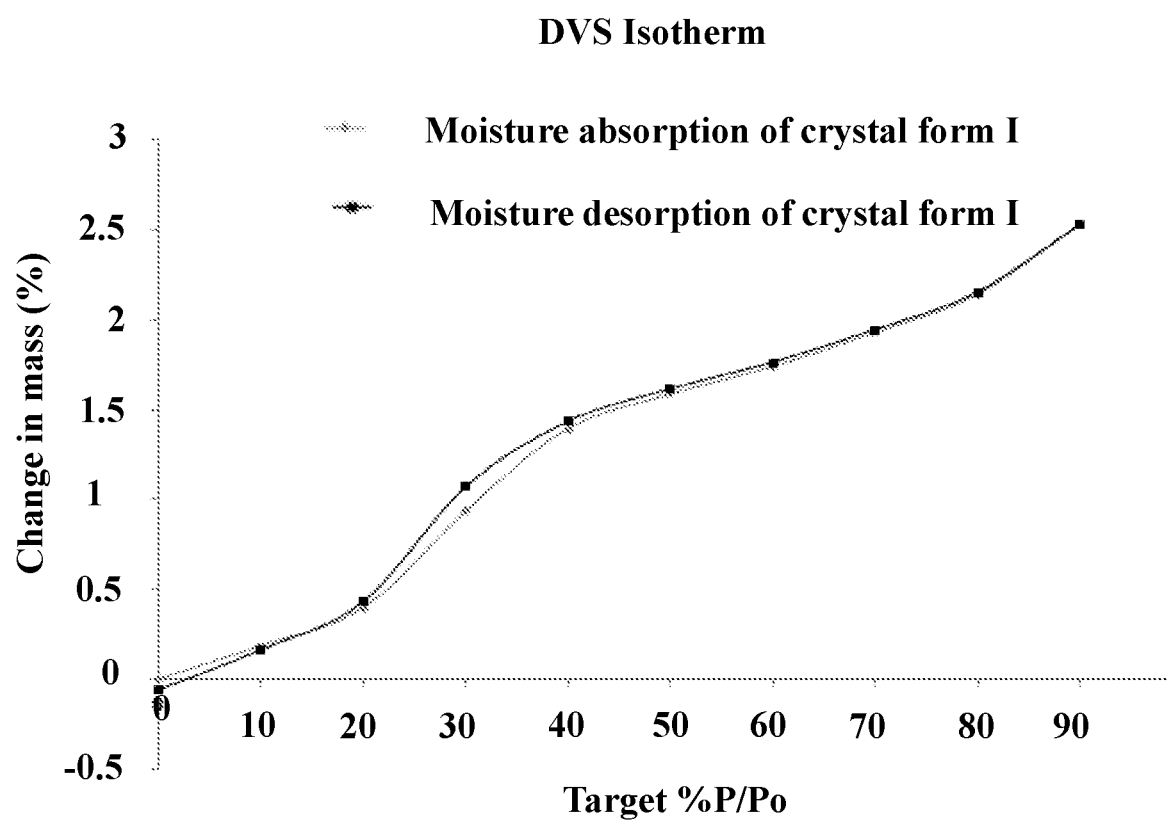
FIG. 20: the DVS isotherm of the crystal form I of the compound of formula (III).

The DVS pattern of the crystal form I of the compound of formula (III) is as shown in FIG. 20, ΔW=2.134%.

Experimental Results

The crystal form I of the compound of formula (III) has a hygroscopic weight gain of 2.134% at 25±1° C. and 80±2% RH, which is hygroscopic.

TEST EXAMPLE 4: HYGROSCOPICITY TEST OF THE CRYSTAL FORM J OF THE COMPOUND OF FORMULA (IV)

Experimental Materials

SMS DVS Advantage dynamic vapor sorption analyzer

Experimental Method 10 to 15 mg of the crystal form J of the compound of formula (IV) was taken and placed in a DVS sample tray for testing.

Experimental Results

Figure 24:
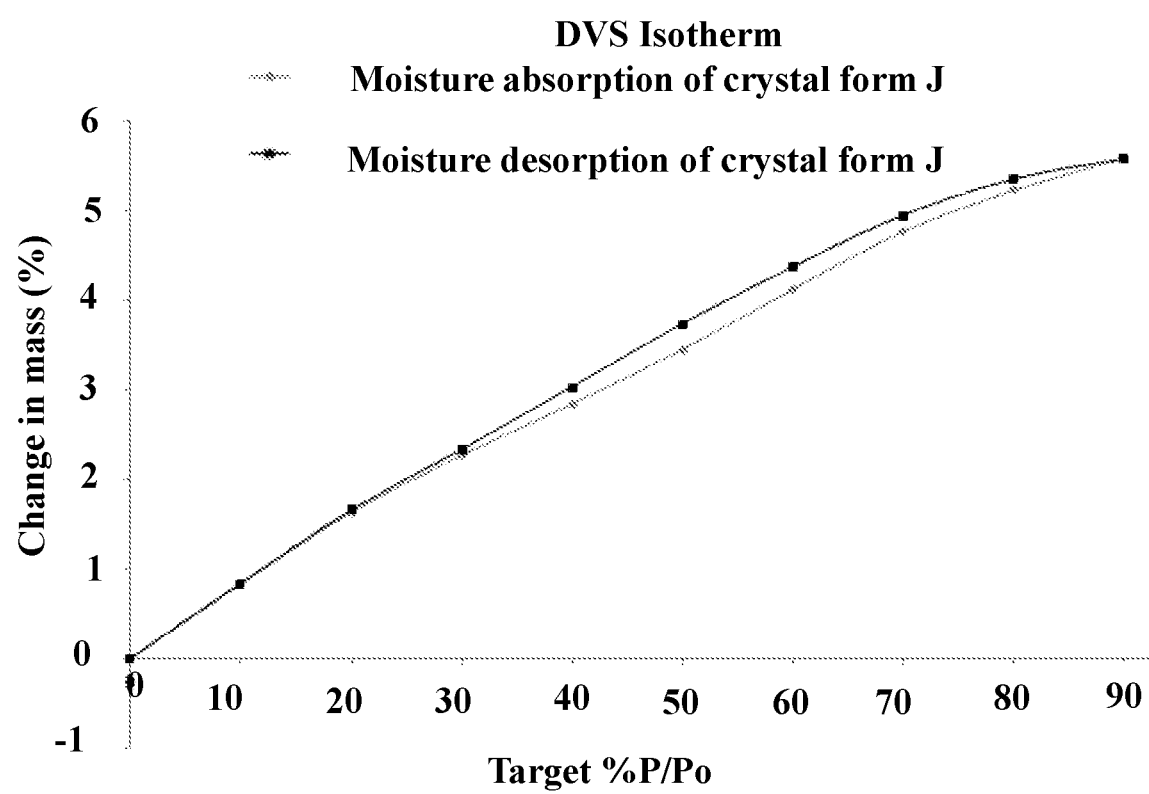
FIG. 24: the DVS isotherm of the crystal form J of the compound of formula (IV).

The DVS pattern of the crystal form J of the compound of formula (IV) is as shown in FIG. 24, ΔW=5.227%.

Experimental Results

The crystal form J of the compound of formula (IV) has a hygroscopic weight gain of 5.227% at 25±1° C. and 80±2% RH, which is hygroscopic.

TEST EXAMPLE 5: IN VITRO ENZYME ACTIVITY TEST OF THE COMPOUND OF THE PRESENT DISCLOSURE

Experimental Purpose

The enzyme activity was detected by Z'-LYTE™ Detection Kinase Assay, and the $IC_{50}$ value of the compound was used as an indicator to evaluate the inhibitory effect of the compound against FGFR1.

Experimental Materials

FGFR1 (Invitrogen #PV4105)
Tyr4 (Invitrogen-PR5053U)
ATP (Sigma-A7699)
DMSO (Sigma cat #34869-100ML)
Reaction buffer solution: 50 mM Hepes (pH 7.5), 10 mM $MgCl_2$, 1 mM EGTA, 0.01% Brij-35, 1 mM DTT, 2 mM $MnCl_2$;
384 Reaction plate (Corning Costar 3573)
384 Compound plate (Greiner #781280)
Development reagent B (Invitrogen #PR5193D)
Development Buffer (Invitrogen #PR4876B)
Centrifuge (Eppendorf #5810R)
Electronic loading gun (Eppendorf)
Multidrop Liquid Workstation (ThermoScientific)
Bravo Automatic Liquid Workstation (Agilent)
Envision (Perkin Elmer)

Experimental Procedures and Methods

A. Preparation of Enzyme/Substrate Mixture 0.6 nM FGFR1, 2 μm Tyr$^4$ peptide and 10 μm ATP in reaction buffer solution (50 mM Hepes, pH 7.5, 10 mM MgCl$_2$, 0.01% BRU-35, 1 mM EGTA, 4 mM MnCl$_2$, 2 mM DTT).

B. Compound Loading a. Diluting the compound with DMSO to 10 mM, 3-fold dilution, 11 gradients, two duplicate wells;

b. Transferring compound diluted with a ratio of 1:25 to the middle plate at Bravo Automatic Liquid Station. Then transferring 2.5 uL to the reaction plate to ensure the final DMSO concentration to be 1%;

c. Transferring 5 μL enzyme/substrate buffer to each well;

d. Adding ATP solution to each well sequentially with Multidrop liquid workstation;

e. Centrifuging at 1000 rpm for 1 minute;

f. Placing the reaction plate in a 23° C. incubator, and allowing to react for 60 minutes.

C. Color Reaction Experiment a. Preparing a mixture of Development regent B and Development Buffer with a ratio of 1:128;

b. Adding 5 uL to each well and centrifuging at 1000 rpm for 1 minute;

c. Placing the reaction plate into an incubator (23° C.) for 90 minutes after centrifugation, taking it out, and reading it in the Envision (Perkin Elmer) plate reader D. Analyzing the Data: using XLFIT (IDBS) to Analyze the Data and Calculating the IC$_{50}$ Value of the Compound The experimental results are shown in Table 17:

TABLE 17

| Z'-LYTE ™ IC$_{50}$ test results | |
|---|---|
| Test sample | FGFR1 |
| Embodiment 1 | AAA |

Note:
50 nM < A ≤ 1 μm, 10 nM < AA ≤ 50 nM, AAA ≤ 10 nM, N/A means not measured.

Conclusion: The compound of the present disclosure has a significant inhibitory effect against FGFR1.

TEST EXAMPLE 6: TUMOR GROWTH INHIBITION (TGI) ANALYSIS OF THE COMPOUND OF THE PRESENT DISCLOSURE

The evolutionary growth potential of tumors was evaluated by the relationship between tumor volume and time. The long axis (L) and short axis (W) of the subcutaneous tumor were measured twice a week by the caliper and the tumor volume (TV) was calculated by the formula ((L×W$^2$)/2). TGI was calculated from the difference between the median tumor volume in the solvent group mice and the median tumor volume in the drug group mice, expressed as a percentage counting for the median tumor volume in the solvent control group, calculated by the following formula:

% $TGI$=((median tumor volume (control)−median tumor volume (dosing group))/median tumor volume (control group))×100

The original statistical analysis was done by repeating the analysis of variance, followed by post-hoc Scheffe's test method for multiple comparisons, with solvent alone (0.5% methylcellulose+0.2% Tween in water) as negative control.

The experimental results are shown in Table 18:

| | FGFR1/2 Highly Expressed Patient-derived Liver Tumor Transplantation Model | TGI % (last administration) |
|---|---|---|
| Embodiment 1 | 5 mg/kg, BID | 85 |

The compound of the present disclosure has excellent in vitro FGFR1 kinase inhibitory activity and can be used as a small molecule tyrosine kinase inhibitor; and it can inhibit cell proliferation and angiogenesis, having excellent antitumor activity, and having excellent results for the treatment of various mammals (including humans).

What is claimed is:

1. A crystal form of a compound of formula (II), (III), or (IV):

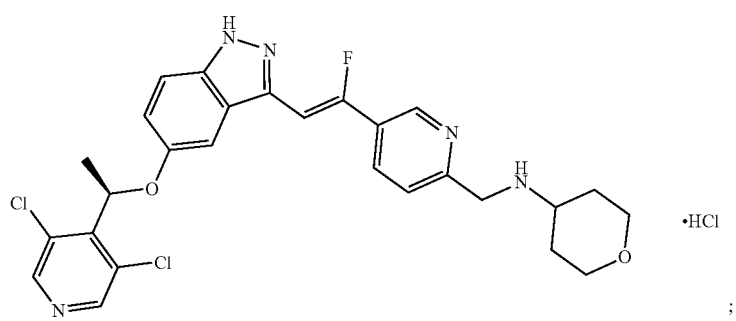

-continued

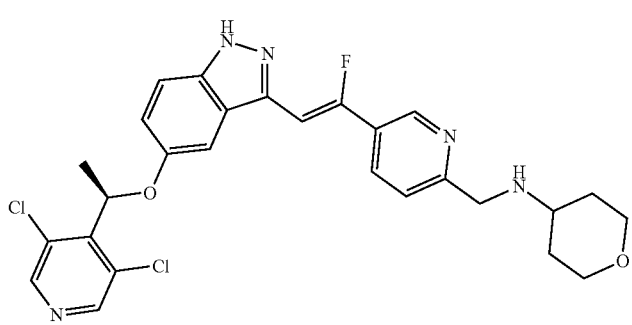 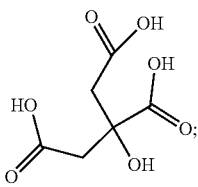

(III)

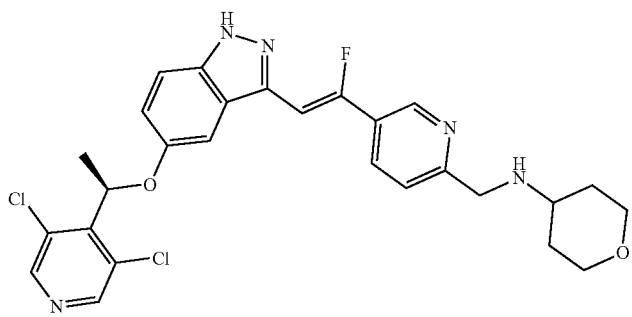 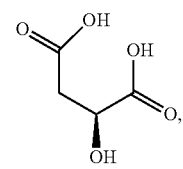

(IV)

wherein the crystal form is a crystal form G of the compound of formula (II) or a crystal form I of the compound of formula (III) or a crystal form J of the compound of formula (IV), wherein:
- the X-ray powder diffraction pattern of the crystal form G of the compound of formula (II) comprises characteristic diffraction peaks at the following angle 2θ: 7.39±0.2°, 19.07±0.2°, and 20.04±0.2°;
- the X-ray powder diffraction pattern of the crystal form I of the compound of formula (III) comprises characteristic diffraction peaks at the following angle 2θ: 6.73±0.2°, 11.66±0.2°, and 19.51±0.2°;
- and the X-ray powder diffraction pattern of the crystal form J of the compound of formula (IV) comprises characteristic diffraction peaks at the following angle 2θ: 4.99±0.2°, 11.32±0.2°, and 19.95±0.2°.

2. The crystal form of the compound of formula (II), (III), or (IV) as defined in claim 1, wherein:
- the X-ray powder diffraction pattern of the crystal form G of the compound of formula (II) comprises characteristic diffraction peaks at the following angle 2θ: 7.39±0.2°, 19.07±0.2°, 20.04±0.2°, 21.05±0.2°, 21.76±0.2°, 25.64±0.2°, 26.23±0.2°, and 27.16±0.2°;
- and/or, the X-ray powder diffraction pattern of the crystal form I of the compound of formula (III) comprises characteristic diffraction peaks at the following angle 2θ: 6.73±0.2°, 11.66±0.2°, 14.28±0.2°, 14.99±0.2°, 16.39±0.2°, 19.51±0.2°, 23.34±0.2°, and 25.61±0.2°;
- and/or, the X-ray powder diffraction pattern of the crystal form J of the compound of formula (IV) comprises characteristic diffraction peaks at the following angle 2θ: 4.99±0.2°, 6.90±0.2°, 9.9±0.2°, 10.73±0.2°, 11.32±0.2°, 14.41±0.2°, 16.73±0.2°, and 19.95±0.2°.

Figure 11:
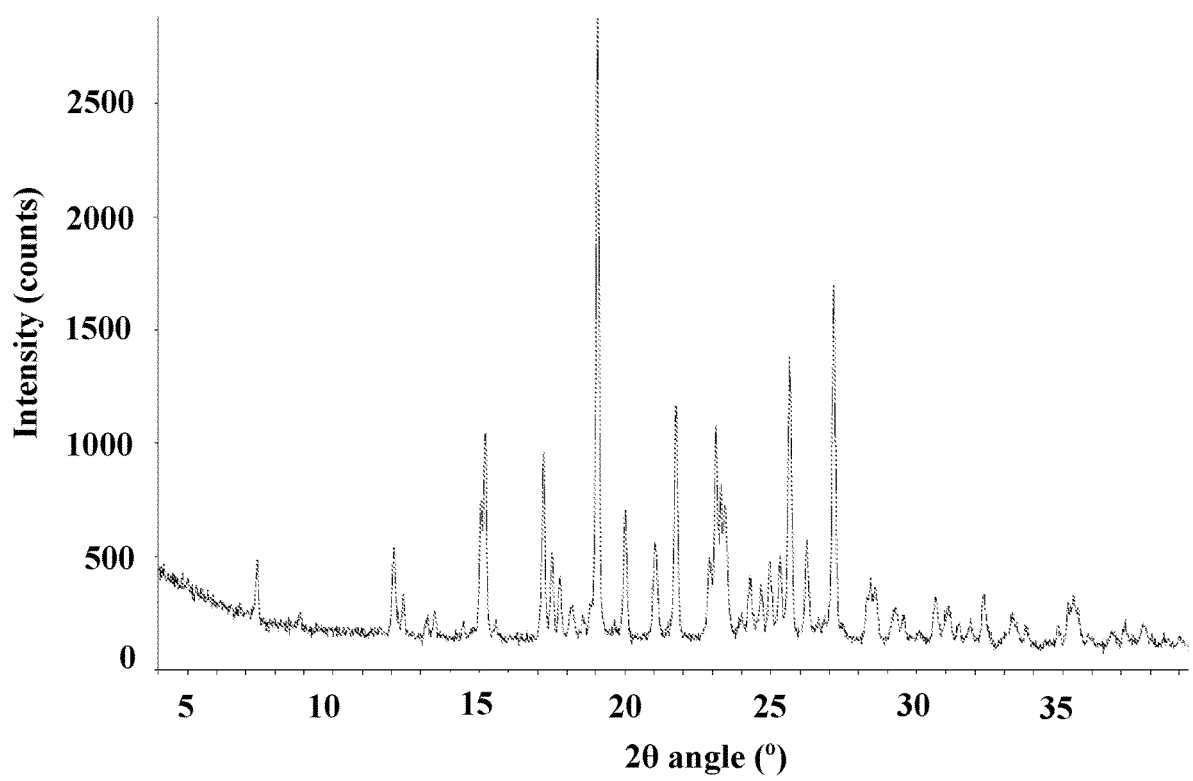
FIG. 11: the XRPD pattern measured by Cu-Kα radiation of the crystal form G of the compound of formula (II).
Figure 17:
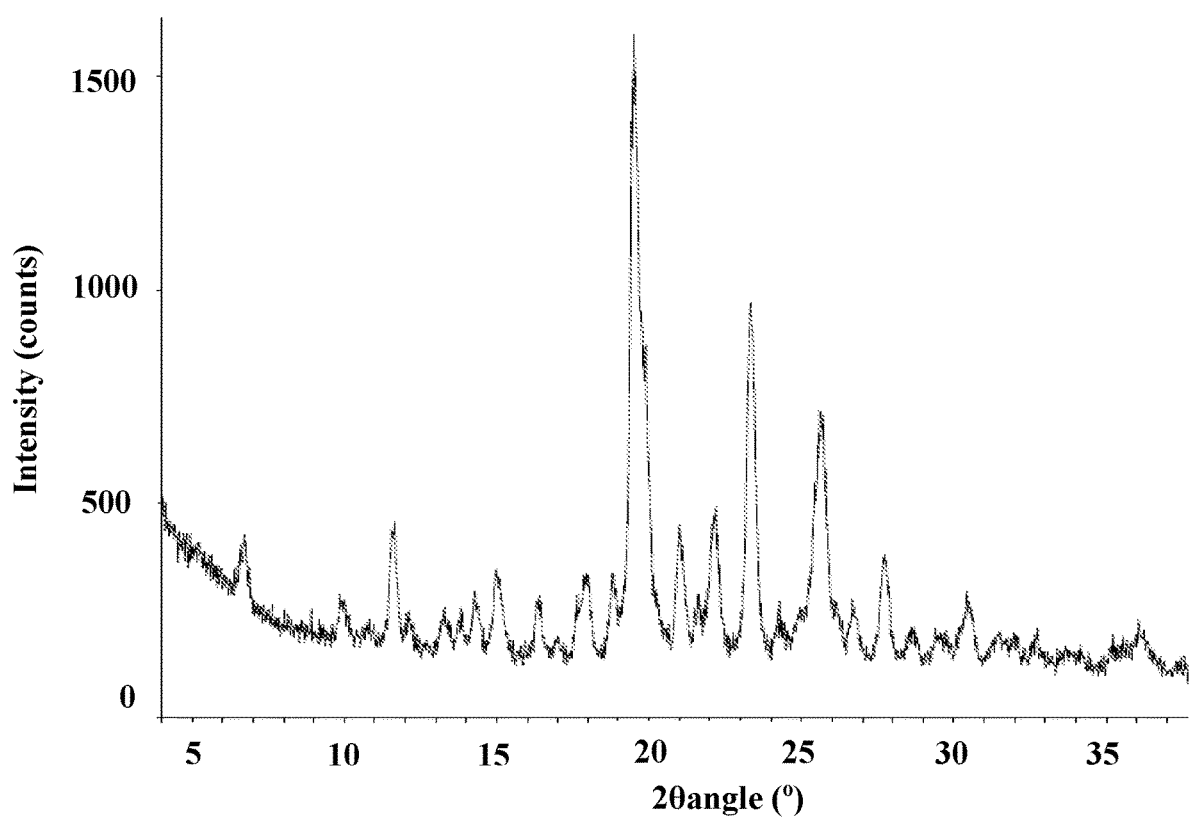
FIG. 17: the XRPD pattern measured by Cu-Kα radiation of the crystal form I of the compound of formula (III).
Figure 21:
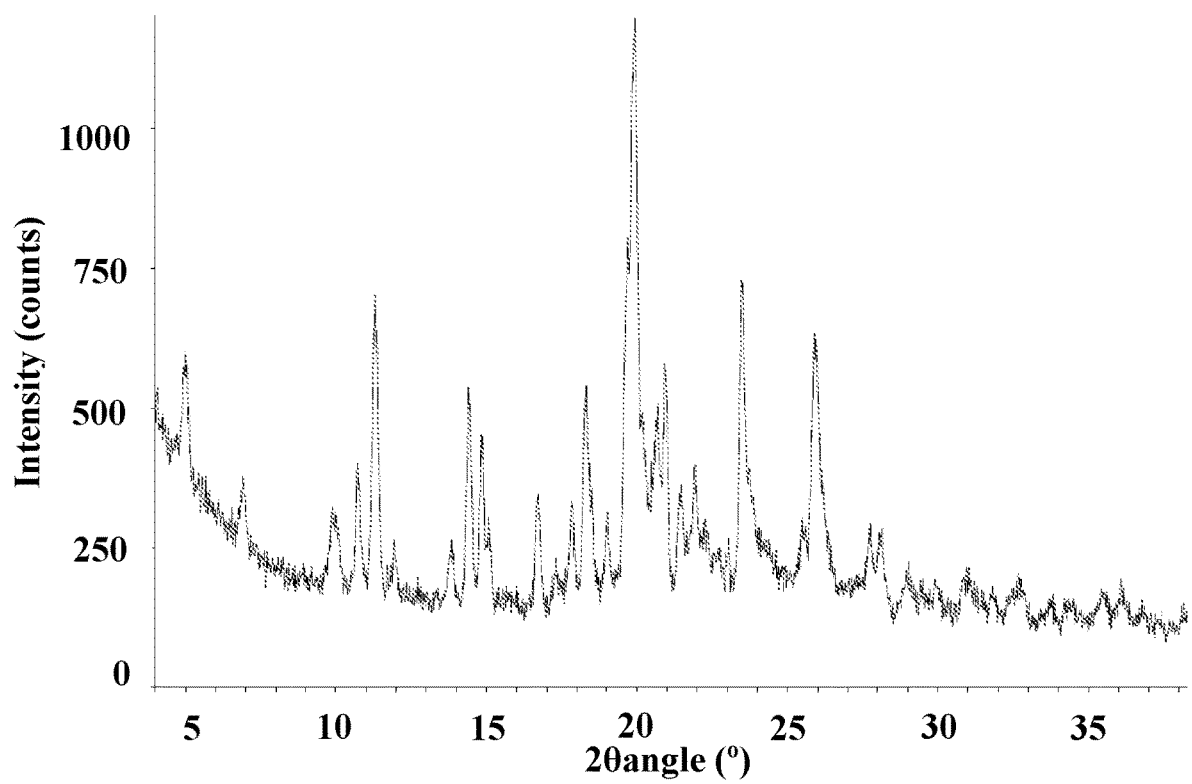
FIG. 21: the XRPD pattern measured by Cu-Kα radiation of the crystal form J of the compound of formula (IV).

3. The crystal form of the compound of formula (II), (III), or (IV) as defined in claim 2, wherein:
- the XRPD pattern of the crystal form G of the compound of formula (II) is as shown in FIG. 11;
- and/or, the XRPD pattern of the crystal form I of the compound of formula (III) is as shown in FIG. 17;
- and/or, the XRPD pattern of the crystal form J of the compound of formula (IV) is as shown in FIG. 21.

4. The crystal form of the compound of formula (II), (III), or (IV) as defined in claim 1, wherein:
- the differential scanning calorimetry curve of the crystal form G of the compound of formula (II) has an onset point of an endothermic peak at 278.70° C.±3° C., and has an onset point of an exothermic peak at 285.46° C.±3° C.;
- and/or, the thermogravimetric analysis curve of the crystal form G of the compound of formula (II) has a weight loss of 3.870% occurred at 120° C.±3° C. and a weight loss of 1.170% occurred at 221.76° C.±3° C.;
- and/or, the differential scanning calorimetry curve of the crystal form I of the compound of formula (III) has an onset point of an endothermic peak at 32.94° C.±3° C. and 204.62° C.±3° C., respectively;
- and/or, the thermogravimetric analysis curve of the crystal form I of the compound of formula (III) has a weight loss of 0.8601% occurred at 85.39° C.±3° C. and a weight loss of 2.264% occurred at 184.93° C.±3° C.;
- and/or, the differential scanning calorimetry curve of the crystal form J of the compound of formula (IV) has an onset point of an endothermic peak at 33.34° C.±3° C. and 194.84° C.±3° C., respectively;
- and/or, the thermogravimetric analysis curve of the crystal form J of the compound of formula (IV) has a weight loss of 1.357% occurred at 120° C.±3° C. and a weight loss of 0.8330% occurred at 177.11° C.±3° C.

Figure 12:
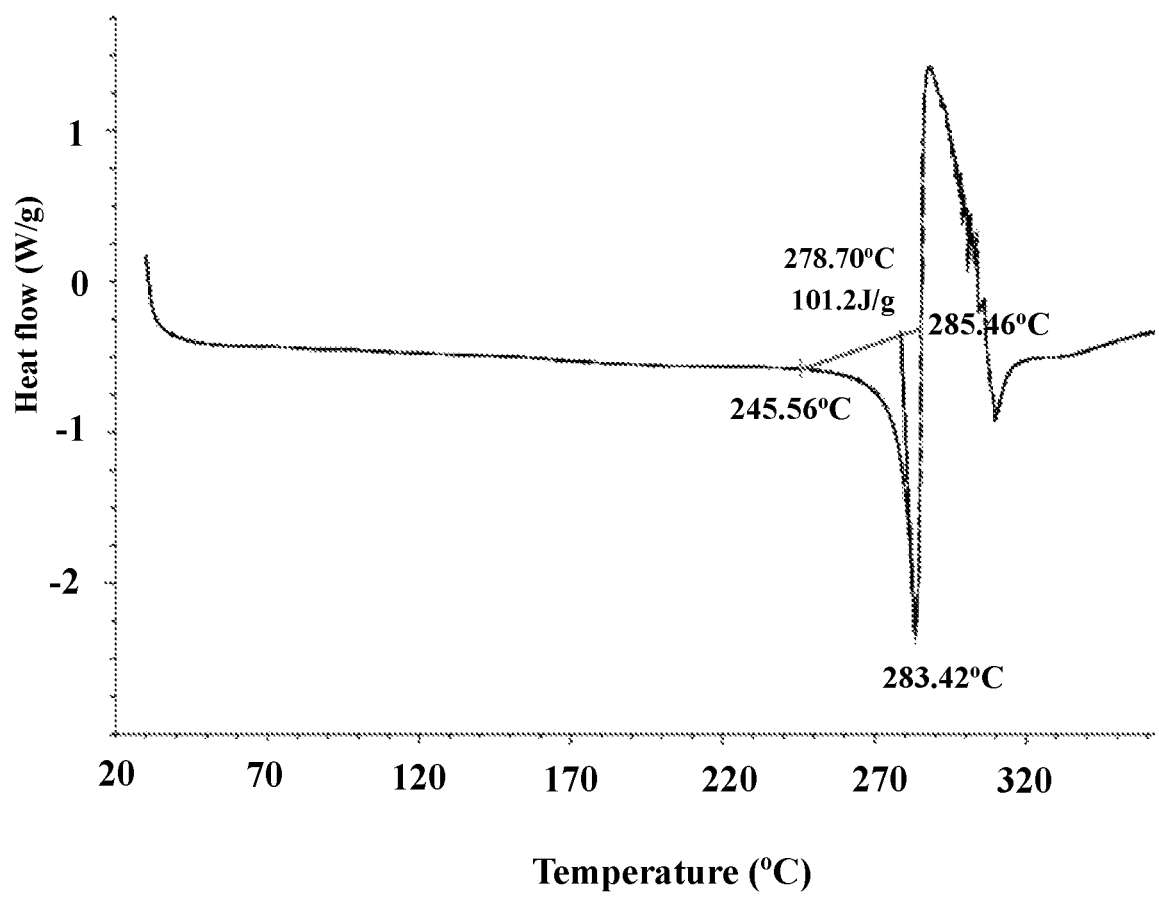
FIG. 12: the DSC pattern of the crystal form G of the compound of formula (II).
Figure 13:
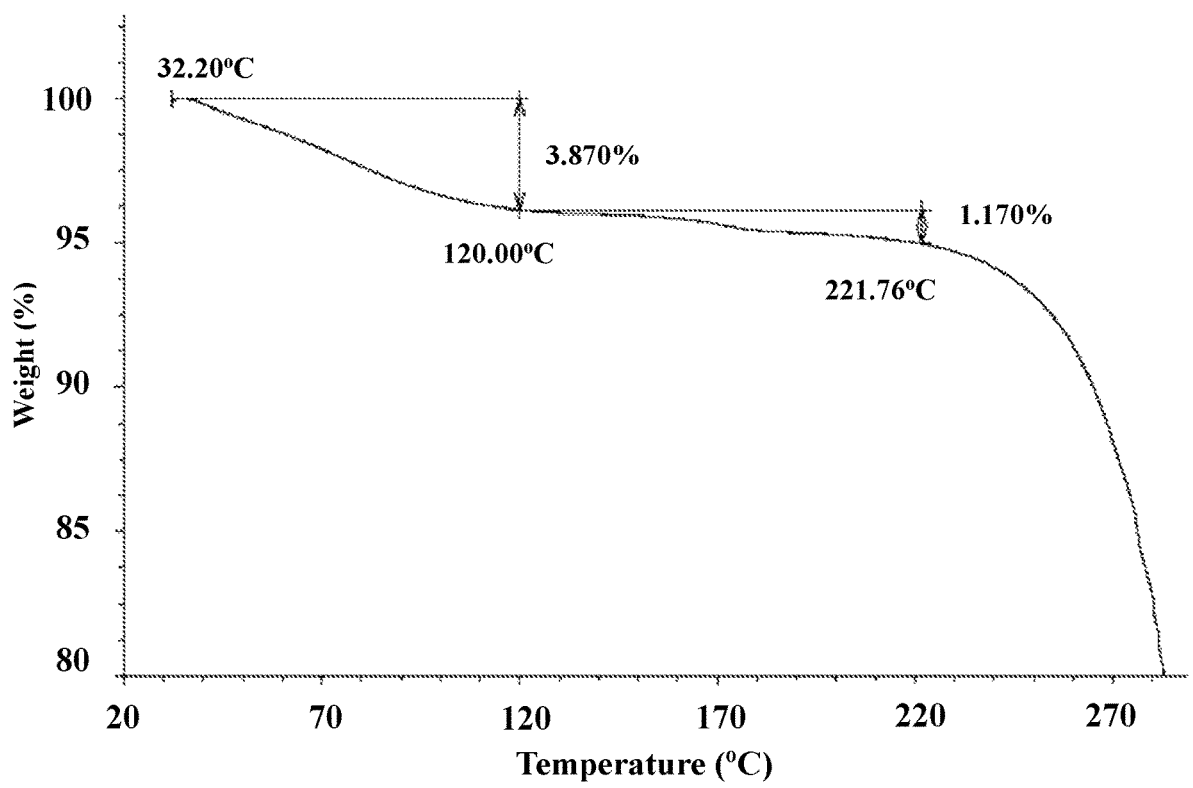
FIG. 13: the TGA pattern of the crystal form G of the compound of formula (II).
Figure 14:
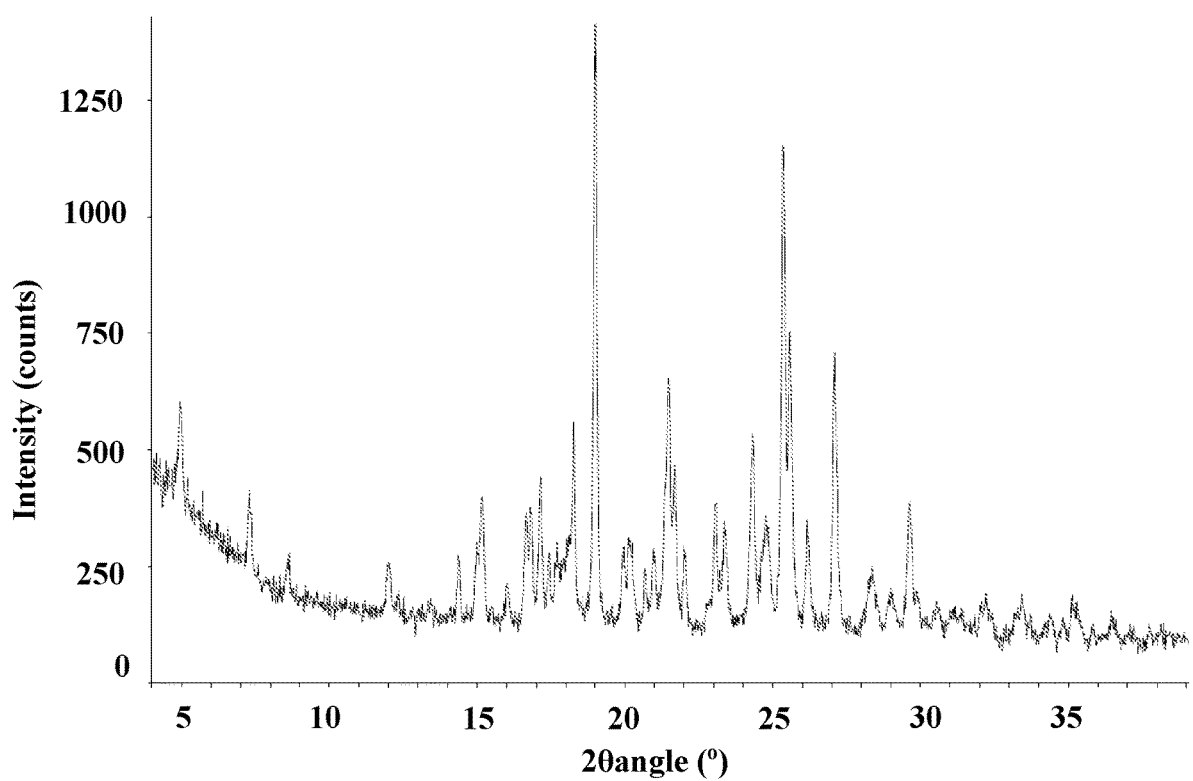
FIG. 14: the XRPD pattern measured by Cu-Kα radiation of the crystal form H of the compound of formula (II).
Figure 15:
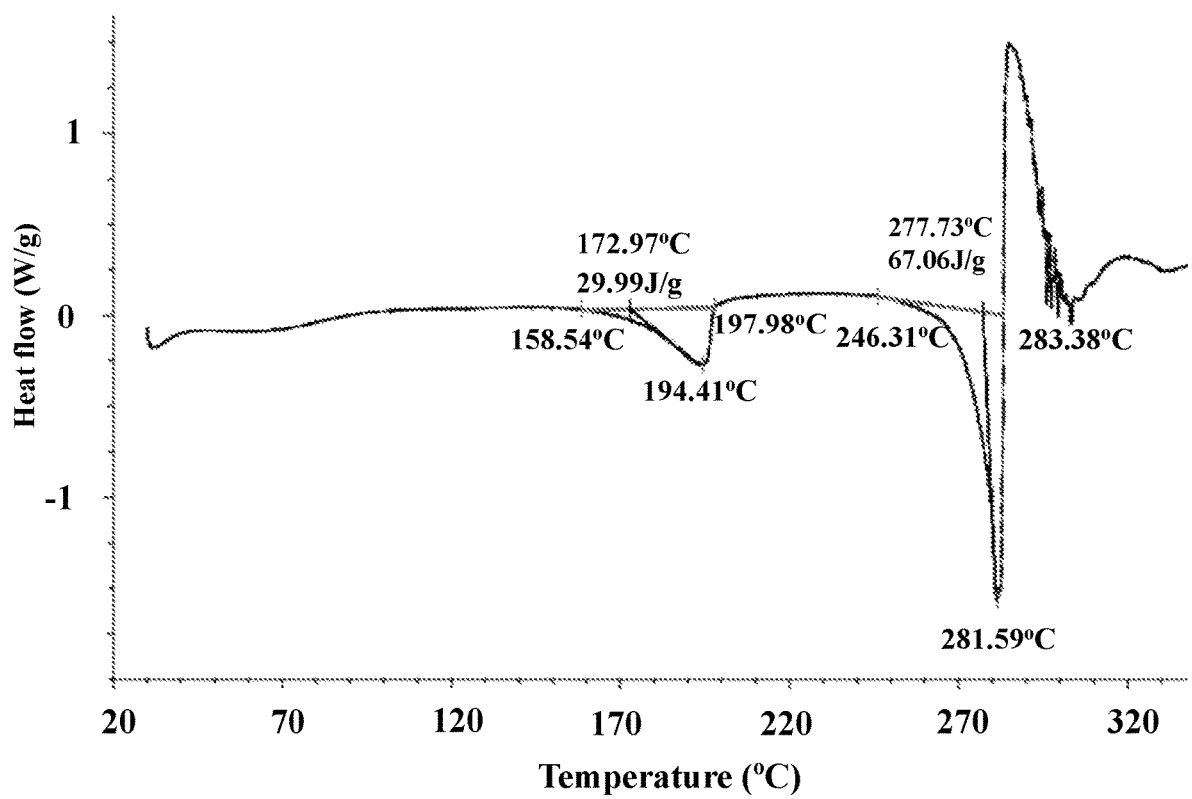
FIG. 15: the DSC pattern of the crystal form H of the compound of formula (II).
Figure 16:
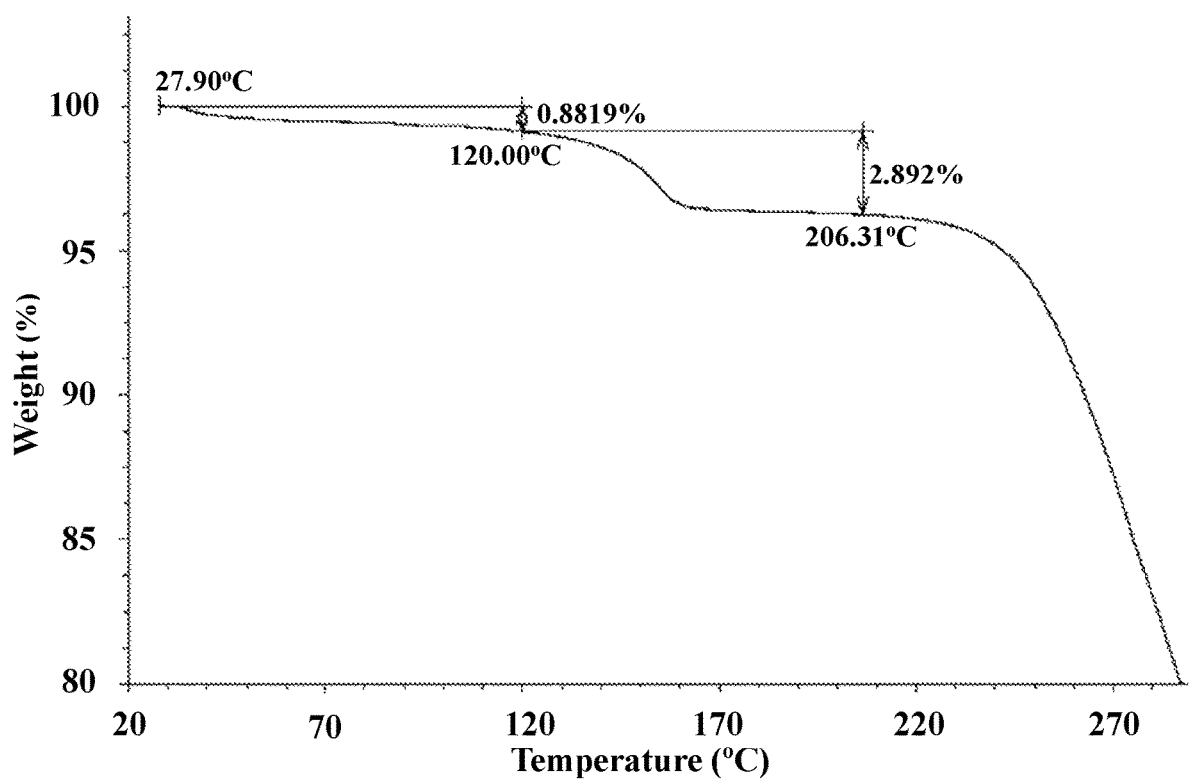
FIG. 16: the TGA pattern of the crystal form H of the compound of formula (II).

5. The crystal form of the compound of formula (II), (III), or (IV) as defined in claim 4, wherein the DSC pattern of the crystal form G of the compound of formula (II) is as shown in FIG. 12;
- and/or, the TGA pattern of the crystal form G of the compound of formula (II) is as shown in FIG. 13.

Figure 18:
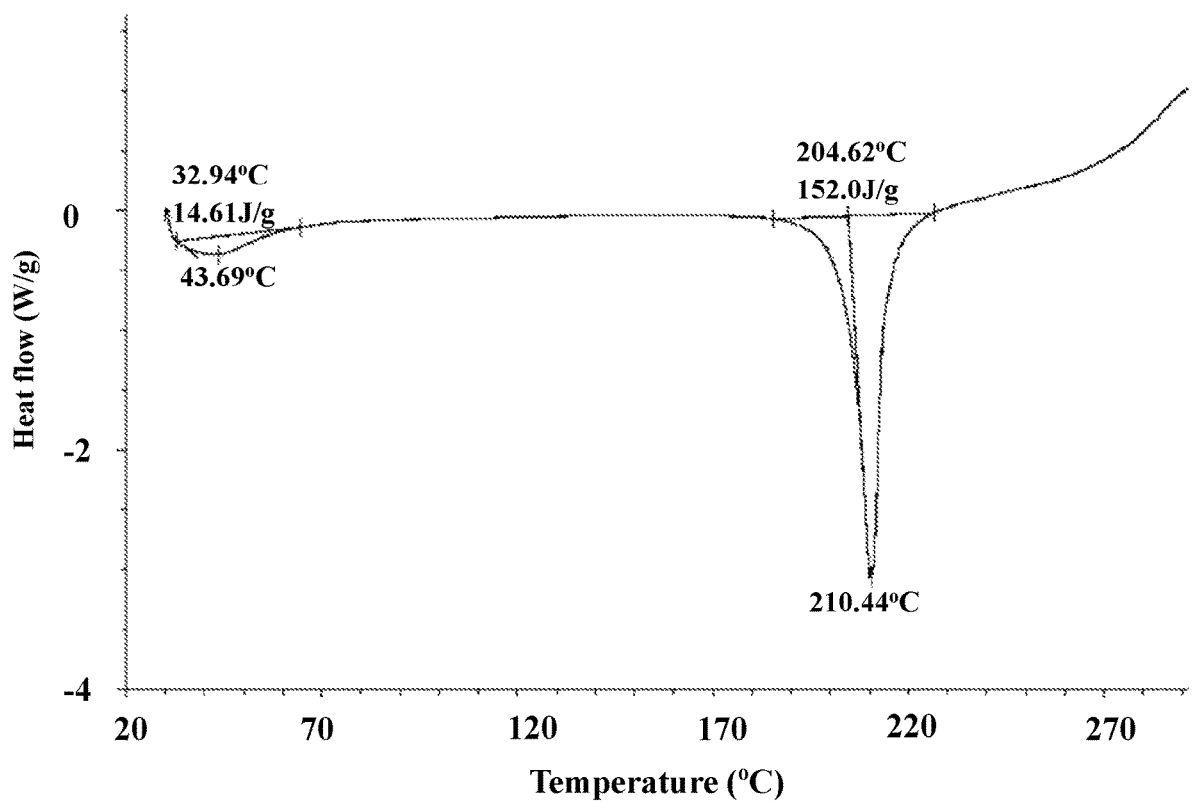
FIG. 18: the DSC pattern of the crystal form I of the compound of formula (III).
Figure 19:
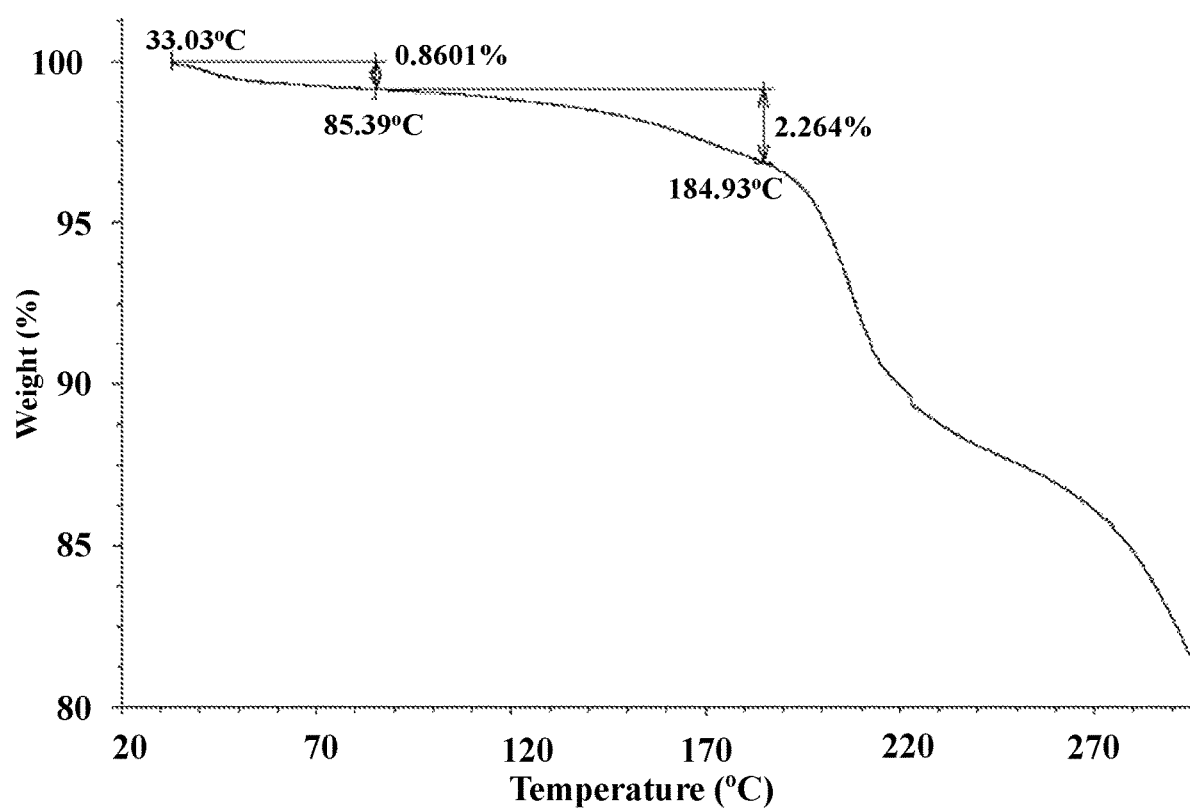
FIG. 19: the TGA pattern of the crystal form I of the compound of formula (III).

6. The crystal form of the compound of formula (II), (III), or (IV) as defined in claim 4, wherein the DSC pattern of the crystal form I of the compound of formula (III) is as shown in FIG. 18;
and/or, the TGA pattern of the crystal form I of the compound of formula (III) is as shown in FIG. 19.

Figure 22:
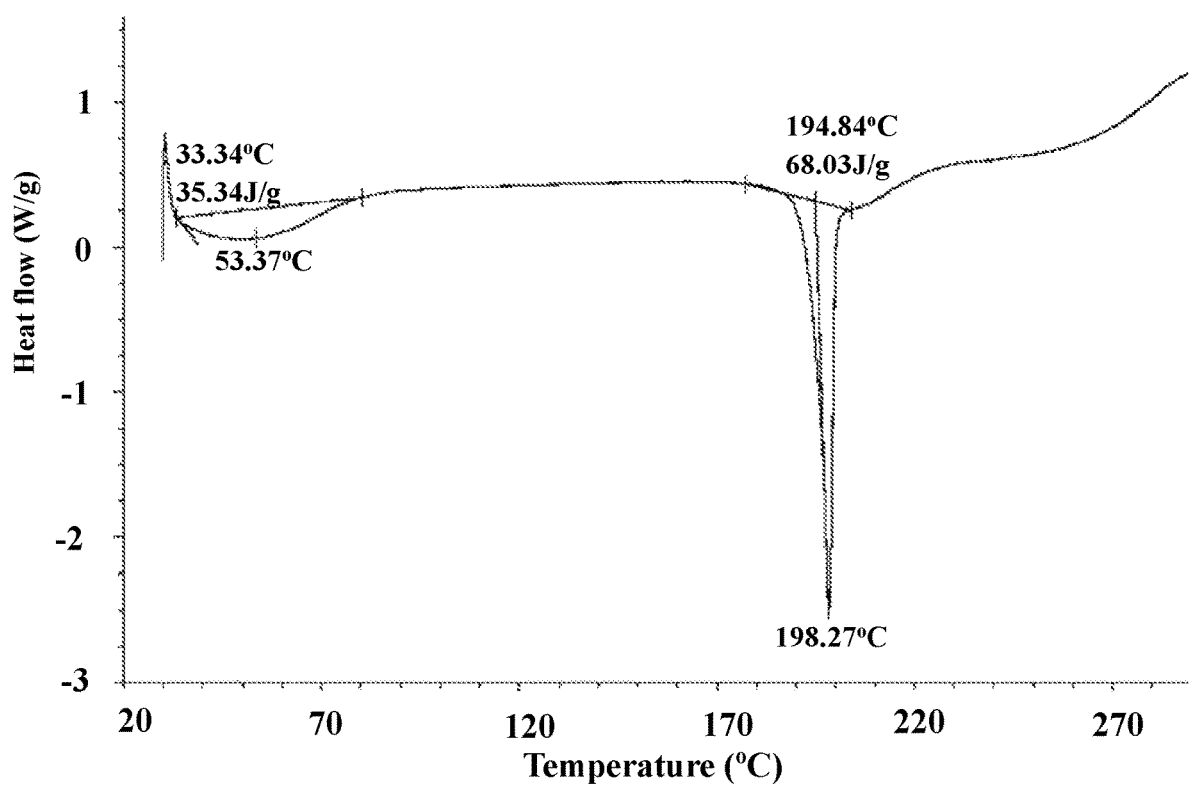
FIG. 22: the DSC pattern of the crystal form J of the compound of formula (IV).
Figure 23:
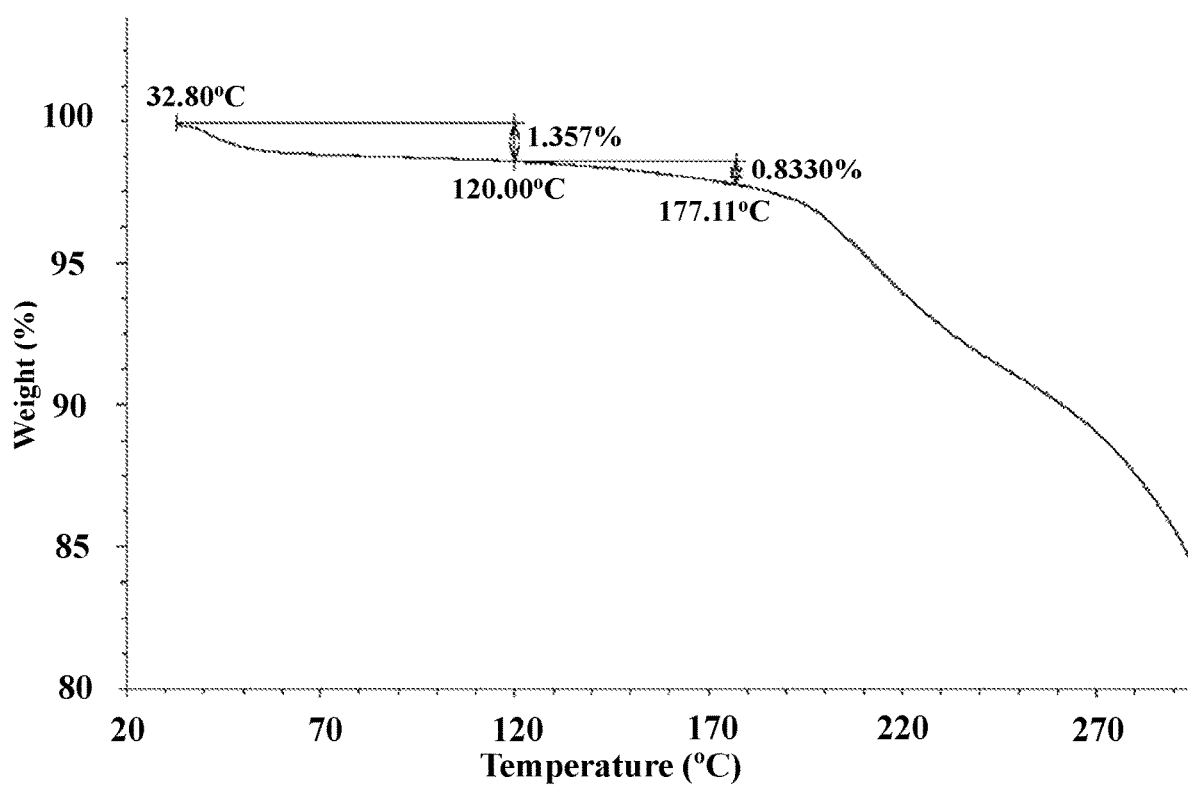
FIG. 23: the TGA pattern of the crystal form J of the compound of formula (IV).

7. The crystal form of the compound of formula (II), (III), or (IV) as defined in claim 4, wherein the DSC pattern of the crystal form J of the compound of formula (IV) is as shown in FIG. 22;
and/or, the TGA pattern of the crystal form J of the compound of formula (IV) is as shown in FIG. 23.

8. A process for preparing the crystal form G of the compound of formula (II), as defined in claim 1, the process comprising:
adding the compound of formula (II) into ethanol to form a mixture,
adding hydrochloric acid/ethyl acetate dropwise to the mixture,
heating and stirring the mixture,
cooling the mixture to room temperature, and
filtering the mixture to obtain the crystal form G of the compound of formula II:

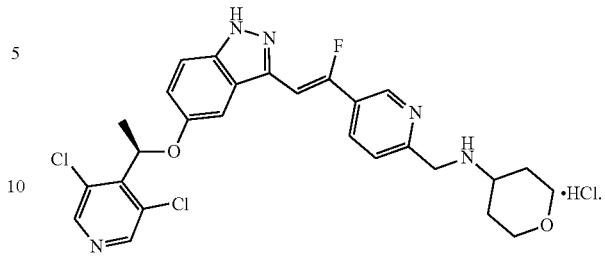

(II)

9. The process as defined in claim 8, wherein the heating and stirring is performed at a temperature of 85° C. to 95° C.

10. A method for inhibiting tyrosine kinase in a subject in need thereof, comprising: administering an effective amount of the crystal form of the compound of formula (II), (III), or (IV) as defined in claim 1 to the subject.

* * * * *